(12) United States Patent
Ishino et al.

(10) Patent No.: US 7,271,311 B2
(45) Date of Patent: Sep. 18, 2007

(54) MAMMALIAN MODEL FOR DIABETES

(75) Inventors: Fumitoshi Ishino, Yokohama (JP); Naoki Miyoshi, Cambridge (GB); Tomoko Ishino, Yokohama (JP); Minesuke Yokoyama, Machida (JP); Shigeharu Wakana, Yokohama (JP)

(73) Assignee: Japan Science and Technology Agency, Kawaguchi-shi, Saitama (JP)

( * ) Notice: Subject to any disclaimer, the term of this patent is extended or adjusted under 35 U.S.C. 154(b) by 286 days.

(21) Appl. No.: 10/252,111

(22) Filed: Sep. 23, 2002

(65) Prior Publication Data

US 2004/0128707 A1 Jul. 1, 2004

Related U.S. Application Data

(63) Continuation-in-part of application No. 10/111,183, filed on Aug. 18, 2000, now abandoned.

(30) Foreign Application Priority Data

Oct. 20, 1999 (JP) ................................. 11-298273

(51) Int. Cl.
*G01N 33/00* (2006.01)
*A01K 67/27* (2006.01)
*A01K 67/33* (2006.01)
(52) U.S. Cl. ............................... 800/3; 800/18; 800/25
(58) Field of Classification Search .................... 800/9, 800/14
See application file for complete search history.

(56) References Cited

FOREIGN PATENT DOCUMENTS

| WO | WO96/32087 | 10/1996 |
|---|---|---|
| WO | WO9637612 | 11/1996 |
| WO | WO 01/28321 | * 4/2001 |

OTHER PUBLICATIONS

Doetschman T. Interpertation of phenotype in genetically engineered mice. Lab Anim Sci. Apr. 1999;49(2):137-43.*
Holschneider et al. Genotype to phenotype: challenges and opportunities. Int J Dev Neurosci. Oct. 2000;18(6):615-8.*
Monk et al. Duplication of 7p11.2-p13, including GRB10, in Silver-Russell syndrome. Am J Hum Genet. Jan. 2000;66(1):36-46.*
Yoshihashi et al. Imprinting of human GRB10 and its mutations in two patients with Russell-Silver syndrome. Am J Hum Genet. Aug. 2000;67(2):476-82. Epub Jun. 12, 2000.*
Hitchins et al. Maternal repression of the human GRB10 gene in the developing central nervous system; evaluation of the role for GRB10 in Silver-Russell syndrome. Eur J Hum Genet. Feb. 2001;9(2):82-90.*
Shiura et al. Meg1/Grb10 overexpression causes postnatal growth retardation and insulin resistance via negative modulation of the IGF1R and IR cascades. Biochem Biophys Res Commun. Apr. 15, 2005;329(3):909-16.*

O'Neill et al. Interaction of a GRB-IR splice variant (a human GRB10 homolog) with the insulin and insulin-like growth factor I receptors. Evidence for a role in mitogenic signaling. J Biol Chem. Sep. 13, 1996;271(37):22506-13.*
Sarani et al., "Nuclear Transplantation in the Mouse: Heritable Difference between Parental Genomes after Activation of the Embryonic Genome", *Cell*, vol. 45, Apr. 1986, pp. 127-136.
McGrath et al., "Completion of Mouse Embryogenesis Requires Both the Maternal and Paternal Genomes", *Cell*, vol. 37, May 1984, pp. 179-183.
DeChiara et al., "Parental Imprinting of the Mouse Insulin-like Growth Factor II Gene", *Cell*, vol. 64, Feb. 22, 1991, pp. 849-859.
Cattanach et al., "Differential Activity of Maternally and Paternally Derived Chromosome Regions In Mice", *Nature*, vol. 315, Jun. 6, 1985, pp. 496-498.
Cattanach et al., "Genomic Imprinting In The Mouse: Possible Final Analysis," found in book entitled *Frontiers in Molecular Biology*, IRL Press, Oxford, 1997, pp. 118-145 (as well as a copy of the cover of the book and print information pages).
Reik, "Genomic Imprinting and Genetic Disorders in Man", *Trends Genet*, vol. 5, No. 10, Oct. 1989, pp. 331-336.
Sapienza, "Genome Imprinting and Cancer Genetics", *Seminars in Cancer Biology*, vol. 3, 1992, pp. 151-158.
Ledbetter et al., "Uniparental Disomy In Humans: Development of an Imprinting Map and Its Implications for Prenatal Diagnosis", *Human Molecular Genetics*, vol. 4, 1995, pp. 1757-1764.
Hurst et al., "Growth Effects of Uniparental Disomies and the Conflict Theory of Genomic Imprinting", *Trends Genet*, vol. 13, No. 11, Nov. 1997, pp. 436-443.
Ooi, et al., "The Cloning of Grb10 Reveals a New Family of SH2 Domain Proteins", *Oncogene*, vol. 10, 1995, pp. 1621-1630.

(Continued)

*Primary Examiner*—Daniel M. Sullivan
(74) *Attorney, Agent, or Firm*—Venable LLP; Ann S. Hobbs; Robert Kinberg

(57) ABSTRACT

An object of the present invention is to provide a model mammal for diabetes onset, being useful for elucidating the onset mechanism of diabetes caused by a blockage of signal transduction from insulin, and for the development of a remedy for said diabetes, and to provide a screening method of a remedy for said diabetes. A diabetic-prone transgenic mouse is prepared in a process comprising the steps of: a transgene that contains a Meg1/Grb10 gene, an imprinted gene exhibiting maternal expression, or a human GRB10 gene in the downstream of a chicken β-actin promoter and in the upstream of a rabbit β-globin poly A is constructed, and subsequently the transgene is microinjected into a male proneucleus of a mouse fertilized egg; thus obtained egg cell is cultured and then transplanted into an oviduct of a pseudopregnant female mouse; after rearing up the recipient animal, baby mice that have the above-mentioned cDNA are selected from the mice born from the recipient animal.

7 Claims, 1 Drawing Sheet

OTHER PUBLICATIONS

Miyoshi et al., "Identification of the *MegIIGrb10* Imprinted Gene on Mouse Proximal Chromosome 11, A Candidate for the Silver-Russell Syndrome Gene", *Proc. Natl. Acad. Sci. USA*, vol. 95, Feb. 1998, pp. 1102-1107.

Jerome et al., "Assignment of Growth Factor Receptor-Bound Protein 10 (*GRB10*) to Human Chromosome 7p11.2-p12", *Genomics*, vol. 40, 1997, pp. 215-216.

Barton et al., "Manupulations of Genetic Constitution by Nuclear Transplantation", *Methods in Enzymology*, vol. 225, 1993, pp. 732-744.

Kaneko-Ishino et al., "*PegI/Mest* Imprinted Gene on Chromosome 6 Identified By cDNA Substraction Hybridization", *Nature Genetics*, vol. 11, Sep. 1995, pp. 52-59.

Niwa et al., "Efficient Selection for Hig-Expression Transfectants With a Novel Eukaryotic Vector", *Gene*, vol. 108, 1991, pp. 193-200.

Shiratori et al., "Gene Therapy for Hepatic Micrometastasis of Murine Colon Carcinoma", *Journal of Hepatology*, vol. 28, 1998, pp. 886-895.

Vollenweider—Insulin Resistant States and Insulin Signaling, Clin Chem Lab Med 2003; 41(9); 1107-1119.

Mattson, Bran Evolution and Lifespan Regulation; Conservation of Signal Transduction pathways that regulate energy metabolism, Mechanisms of Ageing and Development 123 (2002) 947-953.

Di Paola at., Association of hGrb 10 Genetic Variations with Type 2 Diabetes in Caucasian Subjects, Diabetes Care, vol. 29, No. 5, May 2006.

Tatar et al., The Endocrine Regulation of Aging by Insulin-like Signals, Feb. 28, 2003, vol. 299, Science, www.sciencemag.org.

\* cited by examiner

SEQUENCE LISTING

<160> NUMBER OF SEQ ID NOS: 12

<210> SEQ ID NO 1
<211> LENGTH: 1791
<212> TYPE: DNA
<213> ORGANISM: Mouse
<220> FEATURE:
<221> NAME/KEY: CDS
<222> LOCATION: (1)..(1791)

<400> SEQUENCE: 1

```
atg aac aac gat att aac tcg tcc gtg gaa agc ctt aac tca gct tgc        48
Met Asn Asn Asp Ile Asn Ser Ser Val Glu Ser Leu Asn Ser Ala Cys
 1               5                  10                  15 aac atg cag tct gat act gat act gca cca ctt ctt gag gat ggc cag        96
Asn Met Gln Ser Asp Thr Asp Thr Ala Pro Leu Leu Glu Asp Gly Gln
            20                  25                  30 cat gcc agc aac cag gga gca gca tct agc tcc cgg gga cag cca cag       144
His Ala Ser Asn Gln Gly Ala Ala Ser Ser Ser Arg Gly Gln Pro Gln
        35                  40                  45 gcg tcc ccg agg cag aaa atg caa cgc tcg cag cct gtg cac att ctc       192
Ala Ser Pro Arg Gln Lys Met Gln Arg Ser Gln Pro Val His Ile Leu
    50                  55                  60
```

-continued

```
agg cgc ctt cag gag gaa gac cag cag tta aga act gca tct ctt ccg      240
Arg Arg Leu Gln Glu Glu Asp Gln Gln Leu Arg Thr Ala Ser Leu Pro
 65                  70                  75                  80 gcc atc ccc aac cca ttt ccg gag ctc act ggt gcg gcc cct ggg agc      288
Ala Ile Pro Asn Pro Phe Pro Glu Leu Thr Gly Ala Ala Pro Gly Ser
                 85                  90                  95 cct cct tcg gtt gct cct agc tcc tta cct cct cct ccg agc cag cca      336
Pro Pro Ser Val Ala Pro Ser Ser Leu Pro Pro Pro Pro Ser Gln Pro
            100                 105                 110 cct gcc aag cat ttc cct cca ggc ttt cag ctg tcg aaa ctc acc cgt      384
Pro Ala Lys His Phe Pro Pro Gly Phe Gln Leu Ser Lys Leu Thr Arg
        115                 120                 125 cca ggt ctg tgg aca aag acc act gcg aga ttt tca aag aaa caa cct      432
Pro Gly Leu Trp Thr Lys Thr Thr Ala Arg Phe Ser Lys Lys Gln Pro
    130                 135                 140 aag aac cag tgt cca acc gac act gtg aat cca gtg gca cgg atg ccc      480
Lys Asn Gln Cys Pro Thr Asp Thr Val Asn Pro Val Ala Arg Met Pro
145                 150                 155                 160 act tca cag atg gag aag ctg agg ctc aga aag gat gtc aaa gtc ttt      528
Thr Ser Gln Met Glu Lys Leu Arg Leu Arg Lys Asp Val Lys Val Phe
                165                 170                 175 agt gaa gat ggg acc agc aaa gtg gtg gag att cta acc gac atg aca      576
Ser Glu Asp Gly Thr Ser Lys Val Val Glu Ile Leu Thr Asp Met Thr
            180                 185                 190 gcc agg gac ttg tgc cag ctg ctg gtt tac aaa agt cac tgt gtg gat      624
Ala Arg Asp Leu Cys Gln Leu Leu Val Tyr Lys Ser His Cys Val Asp
        195                 200                 205 gac aac agc tgg act tct gtg gaa cac cac cca caa ctg gga tta gag      672
Asp Asn Ser Trp Thr Ser Val Glu His His Pro Gln Leu Gly Leu Glu
    210                 215                 220 agg tgc ctg gag gac cat gag atc gtg gtc caa gtg gag agt acc atg      720
Arg Cys Leu Glu Asp His Glu Ile Val Val Gln Val Glu Ser Thr Met
225                 230                 235                 240 cca agt gag acg aaa ttc tta ttc aga aag att aat gcg aag tac gag      768
Pro Ser Glu Thr Lys Phe Leu Phe Arg Lys Ile Asn Ala Lys Tyr Glu
                245                 250                 255 ttc ttt aag aat cca gtg aac ttc ttc ccg gat cag atg gtc aat tgg      816
Phe Phe Lys Asn Pro Val Asn Phe Phe Pro Asp Gln Met Val Asn Trp
            260                 265                 270 tgc cag cag ccc aac ggt ggc aag gcg cag ctt ctg cag aat ttt ctg      864
Cys Gln Gln Pro Asn Gly Gly Lys Ala Gln Leu Leu Gln Asn Phe Leu
        275                 280                 285 aac acc agc agc tgc cct gag atc cag ggg ttc ttg cag gtg aaa gag      912
Asn Thr Ser Ser Cys Pro Glu Ile Gln Gly Phe Leu Gln Val Lys Glu
    290                 295                 300 gta gga cgc aag tct tgg aag aag ctg tat gtg tgc ctg cgc aga tct      960
Val Gly Arg Lys Ser Trp Lys Lys Leu Tyr Val Cys Leu Arg Arg Ser
305                 310                 315                 320 ggc ctc tat tac tcc acc aag ggg act tca aaa gaa ccc aga cac ctg     1008
Gly Leu Tyr Tyr Ser Thr Lys Gly Thr Ser Lys Glu Pro Arg His Leu
                325                 330                 335 cag ctg ctg gct gac ctg gaa gaa agc agc atc ttc tac ctg att gct     1056
Gln Leu Leu Ala Asp Leu Glu Glu Ser Ser Ile Phe Tyr Leu Ile Ala
            340                 345                 350 gga aag aag cag tac aac gcg ccg aat gaa cat ggg atg tgc atc aag     1104
Gly Lys Lys Gln Tyr Asn Ala Pro Asn Glu His Gly Met Cys Ile Lys
        355                 360                 365 cca aac aaa gcg aag acc gag atg aag gag ctt cgt ctg ctc tgt gcc     1152
Pro Asn Lys Ala Lys Thr Glu Met Lys Glu Leu Arg Leu Leu Cys Ala
```

-continued

```
            370                 375                 380
gaa gat gag cag atc cgt act tgc tgg atg act gcc ttc aga ctg ctc        1200
Glu Asp Glu Gln Ile Arg Thr Cys Trp Met Thr Ala Phe Arg Leu Leu
385                 390                 395                 400 aag tac gga atg ctc ctg tac caa aac tat cgc atc cca cag agg aag        1248
Lys Tyr Gly Met Leu Leu Tyr Gln Asn Tyr Arg Ile Pro Gln Arg Lys
                405                 410                 415 ggt ctg ccc cct cct ttc aac gca cct atg cgc agt gtt tct gag aat        1296
Gly Leu Pro Pro Pro Phe Asn Ala Pro Met Arg Ser Val Ser Glu Asn
            420                 425                 430 tct ctt gtg gcc atg gat ttt tct gga caa atc gga aga gtg atc gat        1344
Ser Leu Val Ala Met Asp Phe Ser Gly Gln Ile Gly Arg Val Ile Asp
        435                 440                 445 aac ccg gcc gaa gcc cag agt gct gcc ctg gaa gag ggc cat gcc tgg        1392
Asn Pro Ala Glu Ala Gln Ser Ala Ala Leu Glu Glu Gly His Ala Trp
    450                 455                 460 cgt aac ggg aga aca cgg atg aat atc cta agc agc caa agc cca ctg        1440
Arg Asn Gly Arg Thr Arg Met Asn Ile Leu Ser Ser Gln Ser Pro Leu
465                 470                 475                 480 cat cct tct acc ctg aat gca gtg att cac agg act cag cat tgg ttc        1488
His Pro Ser Thr Leu Asn Ala Val Ile His Arg Thr Gln His Trp Phe
                485                 490                 495 cat gga cgt atc tcc cgc gag gag tct cac agg atc atc aag caa caa        1536
His Gly Arg Ile Ser Arg Glu Glu Ser His Arg Ile Ile Lys Gln Gln
            500                 505                 510 ggt ctc gtg gac ggg ctg ttc ctc ctt cgt gac agc cag agt aat cca        1584
Gly Leu Val Asp Gly Leu Phe Leu Leu Arg Asp Ser Gln Ser Asn Pro
        515                 520                 525 aag gcg ttc gta ctg aca ctg tgc cat cac cag aag att aaa aac ttc        1632
Lys Ala Phe Val Leu Thr Leu Cys His His Gln Lys Ile Lys Asn Phe
    530                 535                 540 cag atc tta cct tgc gag gat gat ggg cag acc ttc ttc act ctg gat        1680
Gln Ile Leu Pro Cys Glu Asp Asp Gly Gln Thr Phe Phe Thr Leu Asp
545                 550                 555                 560 gat ggg aac acc aag ttc tcc gat ctg atc cag ctg gtc gac ttc tac        1728
Asp Gly Asn Thr Lys Phe Ser Asp Leu Ile Gln Leu Val Asp Phe Tyr
                565                 570                 575 cag ctc aac aaa ggt gtt ctg ccc tgc aag ctg aaa cac cac tgc atc        1776
Gln Leu Asn Lys Gly Val Leu Pro Cys Lys Leu Lys His His Cys Ile
            580                 585                 590 cgc gtg gcc tta tga                                                    1791
Arg Val Ala Leu
        595
```

<210> SEQ ID NO 2
<211> LENGTH: 596
<212> TYPE: PRT
<213> ORGANISM: Mouse

<400> SEQUENCE: 2

```
Met Asn Asn Asp Ile Asn Ser Ser Val Glu Ser Leu Asn Ser Ala Cys
1               5                   10                  15

Asn Met Gln Ser Asp Thr Asp Thr Ala Pro Leu Leu Glu Asp Gly Gln
            20                  25                  30

His Ala Ser Asn Gln Gly Ala Ala Ser Ser Arg Gly Gln Pro Gln
        35                  40                  45

Ala Ser Pro Arg Gln Lys Met Gln Arg Ser Gln Pro Val His Ile Leu
    50                  55                  60

Arg Arg Leu Gln Glu Glu Asp Gln Gln Leu Arg Thr Ala Ser Leu Pro
```

-continued

```
                65                  70                  75                  80
Ala Ile Pro Asn Pro Phe Pro Glu Leu Thr Gly Ala Ala Pro Gly Ser
                    85                  90                  95
Pro Pro Ser Val Ala Pro Ser Ser Leu Pro Pro Pro Ser Gln Pro
                100                 105                 110
Pro Ala Lys His Phe Pro Pro Gly Phe Gln Leu Ser Lys Leu Thr Arg
                115                 120                 125
Pro Gly Leu Trp Thr Lys Thr Thr Ala Arg Phe Ser Lys Lys Gln Pro
            130                 135                 140
Lys Asn Gln Cys Pro Thr Asp Thr Val Asn Pro Val Ala Arg Met Pro
145                 150                 155                 160
Thr Ser Gln Met Glu Lys Leu Arg Leu Arg Lys Asp Val Lys Val Phe
                    165                 170                 175
Ser Glu Asp Gly Thr Ser Lys Val Val Glu Ile Leu Thr Asp Met Thr
                180                 185                 190
Ala Arg Asp Leu Cys Gln Leu Leu Val Tyr Lys Ser His Cys Val Asp
            195                 200                 205
Asp Asn Ser Trp Thr Ser Val Glu His His Pro Gln Leu Gly Leu Glu
        210                 215                 220
Arg Cys Leu Glu Asp His Glu Ile Val Val Gln Val Glu Ser Thr Met
225                 230                 235                 240
Pro Ser Glu Thr Lys Phe Leu Phe Arg Lys Ile Asn Ala Lys Tyr Glu
                245                 250                 255
Phe Phe Lys Asn Pro Val Asn Phe Phe Pro Asp Gln Met Val Asn Trp
                260                 265                 270
Cys Gln Gln Pro Asn Gly Gly Lys Ala Gln Leu Leu Gln Asn Phe Leu
            275                 280                 285
Asn Thr Ser Ser Cys Pro Glu Ile Gln Gly Phe Leu Gln Val Lys Glu
        290                 295                 300
Val Gly Arg Lys Ser Trp Lys Lys Leu Tyr Val Cys Leu Arg Arg Ser
305                 310                 315                 320
Gly Leu Tyr Tyr Ser Thr Lys Gly Thr Ser Lys Glu Pro Arg His Leu
                325                 330                 335
Gln Leu Leu Ala Asp Leu Glu Glu Ser Ser Ile Phe Tyr Leu Ile Ala
                340                 345                 350
Gly Lys Lys Gln Tyr Asn Ala Pro Asn Glu His Gly Met Cys Ile Lys
            355                 360                 365
Pro Asn Lys Ala Lys Thr Glu Met Lys Glu Leu Arg Leu Leu Cys Ala
        370                 375                 380
Glu Asp Glu Gln Ile Arg Thr Cys Trp Met Thr Ala Phe Arg Leu Leu
385                 390                 395                 400
Lys Tyr Gly Met Leu Leu Tyr Gln Asn Tyr Arg Ile Pro Gln Arg Lys
                405                 410                 415
Gly Leu Pro Pro Pro Phe Asn Ala Pro Met Arg Ser Val Ser Glu Asn
                420                 425                 430
Ser Leu Val Ala Met Asp Phe Ser Gly Gln Ile Gly Arg Val Ile Asp
            435                 440                 445
Asn Pro Ala Glu Ala Gln Ser Ala Ala Leu Glu Glu Gly His Ala Trp
        450                 455                 460
Arg Asn Gly Arg Thr Arg Met Asn Ile Leu Ser Ser Gln Ser Pro Leu
465                 470                 475                 480
His Pro Ser Thr Leu Asn Ala Val Ile His Arg Thr Gln His Trp Phe
                485                 490                 495
```

```
His Gly Arg Ile Ser Arg Glu Glu Ser His Arg Ile Ile Lys Gln Gln
            500                 505                 510

Gly Leu Val Asp Gly Leu Phe Leu Leu Arg Asp Ser Gln Ser Asn Pro
        515                 520                 525

Lys Ala Phe Val Leu Thr Leu Cys His His Gln Lys Ile Lys Asn Phe
    530                 535                 540

Gln Ile Leu Pro Cys Glu Asp Asp Gly Gln Thr Phe Phe Thr Leu Asp
545                 550                 555                 560

Asp Gly Asn Thr Lys Phe Ser Asp Leu Ile Gln Leu Val Asp Phe Tyr
                565                 570                 575

Gln Leu Asn Lys Gly Val Leu Pro Cys Lys Leu Lys His His Cys Ile
        580                 585                 590

Arg Val Ala Leu
        595

<210> SEQ ID NO 3
<211> LENGTH: 4211
<212> TYPE: DNA
<213> ORGANISM: Artificial Sequence
<220> FEATURE:
<223> OTHER INFORMATION: Description of Artificial Sequence:Designed
                        Recombinant DNA

<400> SEQUENCE: 3
aatattattg aagcatttat cagggttatt gtctcatgag cggatacata tttgaatgta      60
tttagaaaaa taaacaaata ggggttccgc gcacatttcc ccgaaaagtg ccacctggtc     120
gacattgatt attgactagt tattaatagt aatcaattac gggtcatta gttcatagcc      180 catatatgga gttccgcgtt acataactta cggtaaatgg cccgcctggc tgaccgccca     240
acgacccccg cccattgacg tcaataatga cgtatgttcc catagtaacg ccaataggga     300 cttccattg acgtcaatgg gtggactatt tacggtaaac tgcccacttg gcagtacatc      360
aagtgtatca tatgccaagt acgcccccta ttgacgtcaa tgacggtaaa tggcccgcct     420
ggcattatgc ccagtacatg accttatggg actttcctac ttggcagtac atctacgtat     480
tagtcatcgc tattaccatg gtcgaggtg agccccacgt tctgcttcac tctccccatc      540
tcccccccct cccacccccc aattttgtat ttatttattt tttaattatt ttgtgcagcg     600
atggggcggg ggggggggg ggcgcgcgcc aggcggggcg gggcggggcg aggggcgggg      660 cgggggcgagg cggagaggtg cggcggcagc caatcagagc ggcgcgctcc gaaagtttcc   720
ttttatggcg aggcggcggc ggcggcggcc ctataaaaag cgaagcgcgc ggcgggcggg    780
agtcgctgcg ttgccttcgc cccgtgcccc gctccgcgcc gcctcgcgcc gcccgccccg    840
gctctgactg accgcgttac tcccacaggt gagcgggcgg gacggcccct tctcctccggg    900 ctgtaattag cgcttggttt aatgacggct cgtttctttt ctgtggctgc gtgaaagcct   960
taaagggctc cgggagggcc ctttgtgcgg ggggagcgg ctcgggggt gcgtgcgtgt     1020 gtgtgtgcgt ggggagcgcc gcgtgcggcc cgcgctgccc ggcggctgtg agcgctgcgg    1080
gcgcggcgcg gggctttgtg cgctccgcgt gtgcgcgagg ggagcgcggc cggggcggt    1140 gccccgcggt gcgggggggc tgcgagggga acaaaggctg cgtgcggggt gtgtgcgtgg    1200
gggggtgagc aggggtgtg ggcgcggcgg tcgggctgta acccccccct gcacccccct    1260
ccccgagttg ctgagcacgg cccggcttcg ggtgcgggc tccgtgcggg cgtggcgcg     1320 gggctcgccg tgccgggcgg ggggtggcgg caggtgggg tgccgggcgg ggcggggccg    1380
```

-continued

```
cctcgggccg ggagggctc ggggagggg cgcggcggcc ccggagcgcc ggcggctgtc      1440
gaggcgcggc gagccgcagc cattgccttt tatggtaatc gtgcgagagg gcgcagggac      1500
ttcctttgtc ccaaatctgg cggagccgaa atctgggagg cgccgccgca ccccctctag      1560
cgggcgcggg cgaagcggtg cggcgccggc aggaaggaaa tgggcgggga gggccttcgt      1620
gcgtcgccgc gccgccgtcc ccttctccat ctccagcctc ggggctgccg caggggacg       1680 gctgccttcg gggggacgg ggcagggcgg ggttcggctt ctggcgtgtg accggcggct      1740
ctagagcctc tgctaaccat gttcatgcct tcttctttt cctacagctc ctgggcaacg      1800
tgctggttgt tgtgctgtct catcattttg gcaaagaatt cctcgagggc ttcaagtact      1860
aatgaacaac gatattaact cgtccgtgga aagccttaac tcagcttgca acatgcagtc      1920
tgatactgat actgcaccac ttcttgagga tggccagcat gccagcaacc agggagcagc      1980
atctagctcc cggggacagc cacaggcgtc cccgaggcag aaaatgcaac gctcgcagcc      2040
tgtgcacatt ctcaggcgcc ttcaggagga agaccagcag ttaagaactg catctcttcc      2100
ggccatcccc aacccatttc cggagctcac tggtgcggcc cctgggagcc ctccttcggt      2160
tgctcctagc tccttacctc ctcctccgag ccagccacct gccaagcatt tccctccagg      2220
ctttcagctg tcgaaactca cccgtccagg tctgtggaca aagaccactg cgagattttc      2280
aaagaaacaa cctaagaacc agtgtccaac cgacactgtg aatccagtgg cacggatgcc      2340
cacttcacag atggagaagc tgaggctcag aaaggatgtc aaagtcttta gtgaagatgg      2400
gaccagcaaa gtggtggaga ttctaaccga catgacagcc agggacttgt gccagctgct      2460
ggtttacaaa agtcactgtg tggatgacaa cagctggact tctgtggaac accacccaca      2520
actgggatta gagaggtgcc tggaggacca tgagatcgtg gtccaagtgg agagtaccat      2580
gccaagtgag acgaaattct tattcagaaa gattaatgcg aagtacgagt tctttaagaa      2640
tccagtgaac ttcttcccgg atcagatggt caattggtgc cagcagccca acggtggcaa      2700
ggcgcagctt ctgcagaatt ttctgaacac cagcagctgc cctgagatcc aggggttctt      2760
gcaggtgaaa gaggtaggac gcaagtcttg gaagaagctg tatgtgtgcc tgcgcagatc      2820
tggcctctat tactccacca aggggacttc aaaagaaccc agacacctgc agctgctggc      2880
tgacctggaa gaaagcagca tcttctacct gattgctgga aagaagcagt acaacgcgcc      2940
gaatgaacat gggatgtgca tcaagccaaa caaagcgaag accgagatga aggagcttcg      3000
tctgctctgt gccgaagatg agcagatccg tacttgctgg atgactgcct tcagactgct      3060
caagtacgga atgctcctgt accaaaacta tcgcatccca cagaggaagg gtctgccccc      3120 tccttcaac gcacctatgc gcagtgtttc tgagaattct cttgtggcca tggatttttc      3180
tggacaaatc ggaagagtga tcgataaccc ggccgaagcc cagagtgctg ccctggaaga      3240
gggccatgcc tggcgtaacg ggagaacacg gatgaatatc ctaagcagcc aaagccccact     3300 gcatccttct accctgaatg cagtgattca caggactcag cattggttcc atggacgtat      3360
ctcccgcgag gagtctcaca ggatcatcaa gcaacaaggt ctcgtggacg ggctgttcct      3420
ccttcgtgac agccagagta atccaaaggc gttcgtactg acactgtgcc atcaccagaa      3480
gattaaaaac ttccagatct taccttgcga ggatgatggg cagaccttct tcactctgga      3540
tgatgggaac accaagttct ccgatctgat ccagctggtc gacttctacc agctcaacaa      3600
aggtgttctg ccctgcaagc tgaaacacca ctgcatccgc gtggccttat gacctctcga      3660
ggaattcact cctcaggtgc aggctgccta tcagaaggtg gtggctggtg tggccaatgc      3720
cctggctcac aaataccact gagatctttt tccctctgcc aaaaattatg gggacatcat      3780
```

```
gaagcccctt gagcatctga cttctggcta ataaaggaaa tttattttca ttgcaatagt    3840
gtgttggaat tttttgtgtc tctcactcgg aaggacatat gggagggcaa atcatttaaa    3900
acatcagaat gagtatttgg tttagagttt ggcaacatat gccatatgct ggctgccatg    3960
aacaaaggtg gctataaaga ggtcatcagt atatgaaaca gcccctgct gtccattcct     4020 tattccatag aaaagccttg acttgaggtt agattttttt tatattttgt tttgtgttat    4080
tttttctttt aacatcccta aaattttcct tacatgtttt actagccaga ttttccctcc    4140
tctcctgact actcccagtc atagctgtcc ctcttctctt atgaagatcc ctcgacctgc    4200
agcccaagct t                                                         4211

<210> SEQ ID NO 4
<211> LENGTH: 2503
<212> TYPE: DNA
<213> ORGANISM: Homo sapiens
<300> PUBLICATION INFORMATION:

<400> SEQUENCE: 4
ggcgcaactt tggctcccag ggaacaaaca tcctccttct aagtggtaga tgtgggtgag    60
ctgaccctgc tggagtctgt ccctgggct accctctgct tcccccatt gtgagtggtc     120 cgtgaagcac agcgttgacc agacctaagc ctgtttgctc ccaggacaag gtggagcaga   180
cacctcgcag tcaacaagac ccggcaggac caggactccc cgcacagtct gaccgacttg   240
cgaatcacca ggaggatgat gtggacctgg aagccctggt gaacgat atg aat gca     296
                                                    Met Asn Ala
                                                      1 tcc ctg gag agc ctg tac tcg gcc tgc agc atg cag tca gac acg gtg    344
Ser Leu Glu Ser Leu Tyr Ser Ala Cys Ser Met Gln Ser Asp Thr Val
  5                  10                  15 ccc ctc ctg cag aat ggc cag cat gcc cgc agc cag cct cgg gct tca    392
Pro Leu Leu Gln Asn Gly Gln His Ala Arg Ser Gln Pro Arg Ala Ser
 20                  25                  30                  35 ggc cct cct cgg tcc atc cag cca cag gtg tcc ccg agg cag agg gtg    440
Gly Pro Pro Arg Ser Ile Gln Pro Gln Val Ser Pro Arg Gln Arg Val
             40                  45                  50 cag cgc tcc cag cct gtg cac atc ctc gct gtc agg cgc ctt cag gag    488
Gln Arg Ser Gln Pro Val His Ile Leu Ala Val Arg Arg Leu Gln Glu
         55                  60                  65 gaa gac cag cag ttt aga acc tca tct ctg ccg gcc atc ccc aat cct    536
Glu Asp Gln Gln Phe Arg Thr Ser Ser Leu Pro Ala Ile Pro Asn Pro
     70                  75                  80 ttt cct gaa ctc tgt ggc cct ggg agc ccc cct gtg ctc acg ccg ggt    584
Phe Pro Glu Leu Cys Gly Pro Gly Ser Pro Pro Val Leu Thr Pro Gly
 85                  90                  95 tct tta cct ccg agc cag gcc gcc gca aag cag gat gtt aaa gtc ttt    632
Ser Leu Pro Pro Ser Gln Ala Ala Ala Lys Gln Asp Val Lys Val Phe
100                 105                 110                 115 agt gaa gat ggg aca agc aaa gtg gtg gag att cta gca gac atg aca    680
Ser Glu Asp Gly Thr Ser Lys Val Val Glu Ile Leu Ala Asp Met Thr
                120                 125                 130 gcc aga gac ctg tgc caa ttg ctg gtt tac aaa agt cac tgt gtg gat    728
Ala Arg Asp Leu Cys Gln Leu Leu Val Tyr Lys Ser His Cys Val Asp
            135                 140                 145 gac aac agc tgg aca cta gtg gag cac cac ccg cac cta gga tta gag    776
Asp Asn Ser Trp Thr Leu Val Glu His His Pro His Leu Gly Leu Glu
        150                 155                 160 agg tgc ttg gaa gac cat gag ctg gtg gtc cag gtg gag agt acc atg    824
```

-continued

```
            Arg Cys Leu Glu Asp His Glu Leu Val Val Gln Val Glu Ser Thr Met
                165                 170                 175 gcc agt gag agt aaa ttt cta ttc agg aag aat tac gca aaa tac gag       872
Ala Ser Glu Ser Lys Phe Leu Phe Arg Lys Asn Tyr Ala Lys Tyr Glu
180                 185                 190                 195 ttc ttt aaa aat ccc atg aat ttc ttc cca gaa cag atg gtt act tgg       920
Phe Phe Lys Asn Pro Met Asn Phe Phe Pro Glu Gln Met Val Thr Trp
                200                 205                 210 tgc cag cag tca aat ggc agt caa acc cag ctt ttg cag aat ttt ctg       968
Cys Gln Gln Ser Asn Gly Ser Gln Thr Gln Leu Leu Gln Asn Phe Leu
                215                 220                 225 aac tcc agt agt tgt cct gaa att caa ggg ttt ttg cat gtg aaa gag      1016
Asn Ser Ser Ser Cys Pro Glu Ile Gln Gly Phe Leu His Val Lys Glu
                230                 235                 240 ctg gga aag aaa tca tgg aaa aag ctg tat gtg tgt ttg cgg aga tct      1064
Leu Gly Lys Lys Ser Trp Lys Lys Leu Tyr Val Cys Leu Arg Arg Ser
245                 250                 255 ggc ctt tat tgc tcc acc aag gga act tca aag gaa ccc aga cac ctg      1112
Gly Leu Tyr Cys Ser Thr Lys Gly Thr Ser Lys Glu Pro Arg His Leu
260                 265                 270                 275 cag ctg ctg gcc gac ctg gag gac agc aac atc ttc tcc ctg atc gct      1160
Gln Leu Leu Ala Asp Leu Glu Asp Ser Asn Ile Phe Ser Leu Ile Ala
                280                 285                 290 ggc agg aag cag tac aac gcc cct aca gac cac ggg ctc tgc ata aag      1208
Gly Arg Lys Gln Tyr Asn Ala Pro Thr Asp His Gly Leu Cys Ile Lys
                295                 300                 305 cca aac aaa gtc agg aat gaa act aaa gag ctg agg ttg ctc tgt gca      1256
Pro Asn Lys Val Arg Asn Glu Thr Lys Glu Leu Arg Leu Leu Cys Ala
                310                 315                 320 gag gac gag caa acc agg acg tgc tgg atg aca gcg ttc aga ctc ctc      1304
Glu Asp Glu Gln Thr Arg Thr Cys Trp Met Thr Ala Phe Arg Leu Leu
325                 330                 335 aag tat gaa atg ctc ctt tac cag aat tac cga atc cct cag cag agg      1352
Lys Tyr Glu Met Leu Leu Tyr Gln Asn Tyr Arg Ile Pro Gln Gln Arg
340                 345                 350                 355 aag gcc ttg ctg tcc ccg ttc tcg acg cca gtg cgc agt gtc tcc gag      1400
Lys Ala Leu Leu Ser Pro Phe Ser Thr Pro Val Arg Ser Val Ser Glu
                360                 365                 370 aac tcc ctc gtg gca atg gat ttt tct ggg caa aca gga cgc gtg ata      1448
Asn Ser Leu Val Ala Met Asp Phe Ser Gly Gln Thr Gly Arg Val Ile
                375                 380                 385 gag aat ccg gcg gag gcc cag agc gca gcc ctg gag gag ggc cac gcc      1496
Glu Asn Pro Ala Glu Ala Gln Ser Ala Ala Leu Glu Glu Gly His Ala
                390                 395                 400 tgg agg aag cga agc aca cgg atg aac atc cta ggt agc caa agt ccc      1544
Trp Arg Lys Arg Ser Thr Arg Met Asn Ile Leu Gly Ser Gln Ser Pro
405                 410                 415 ctc cac cct tct acc cta agt aca gtg att cac agg aca cag cac tgg      1592
Leu His Pro Ser Thr Leu Ser Thr Val Ile His Arg Thr Gln His Trp
420                 425                 430                 435 ttt cac ggg agg ttc tcc agg gag gaa tcc cac agg atc att aaa cag      1640
Phe His Gly Arg Phe Ser Arg Glu Glu Ser His Arg Ile Ile Lys Gln
                440                 445                 450 caa ggg ctc gtg gat ggg ctt ttt ctc ctc cgt gac agc cag agt aat      1688
Gln Gly Leu Val Asp Gly Leu Phe Leu Leu Arg Asp Ser Gln Ser Asn
                455                 460                 465 cca aag gca ttt gta ctc aca ctg tgt cat cac cag aaa att aaa aat      1736
Pro Lys Ala Phe Val Leu Thr Leu Cys His His Gln Lys Ile Lys Asn
                470                 475                 480
```

-continued

```
ttc cag atc tta cct tgc gag gac gac ggg cag acg ttc ttc agc cta     1784
Phe Gln Ile Leu Pro Cys Glu Asp Asp Gly Gln Thr Phe Phe Ser Leu
485                 490                 495 gat gac ggg aac acc aaa ttc tct gac ctg atc cag ctg gtt gac ttt     1832
Asp Asp Gly Asn Thr Lys Phe Ser Asp Leu Ile Gln Leu Val Asp Phe
500                 505                 510                 515 tac cag ctg aac aaa gga gtc ctg cct tgc aaa ctc aag cac cac tgc     1880
Tyr Gln Leu Asn Lys Gly Val Leu Pro Cys Lys Leu Lys His His Cys
                520                 525                 530 atc cga gtg gcc tta tga ccgcagatgt cctctcggct gaagactgga            1928
Ile Arg Val Ala Leu
                535 ggaagtgaac actggagtga agaagcggtc tgtgcgttgg tgaagaacac acatcgattc   1988 tgcacctggg gacccagagc gagatgggtt tgttcggtgc cagcctacca agattgacta   2048 gtttgttgga cttaaacgac gatttgctgc tgtgaaccca gcagggtcgc ctccctctgc   2108 gtcggccaaa ttggggaggg catggaagat ccagcgaaaa gttgaaaata aactggaatg   2168 atcatcttgg cttgggccgc ttaggaacaa gaaccggaga gaagtgattg gaaatgaact   2228 cttgccctgg aataatcttg acaattaaaa ctgatatgtt tacttttttt gtattgatca   2288 cttttttgga ctccttcttt gttttcaata ttgtattcag cctattgtag gaggggatg    2348 tggcgtttca actcatataa tacagaaaga gttttggaat gggcagattt caaactgaat   2408 atgggtcccc aaatgttccc agagggtcct ccacaacctc tgccgactac acggtgtgg    2468 attcagctcc caaatgacaa acccagccct tccca                              2503
```

<210> SEQ ID NO 5
<211> LENGTH: 536
<212> TYPE: PRT
<213> ORGANISM: Homo sapiens
<300> PUBLICATION INFORMATION:

<400> SEQUENCE: 5

```
Met Asn Ala Ser Leu Glu Ser Leu Tyr Ser Ala Cys Ser Met Gln Ser
1               5                   10                  15

Asp Thr Val Pro Leu Leu Gln Asn Gly Gln His Ala Arg Ser Gln Pro
            20                  25                  30

Arg Ala Ser Gly Pro Pro Arg Ser Ile Gln Pro Gln Val Ser Pro Arg
        35                  40                  45

Gln Arg Val Gln Arg Ser Gln Pro Val His Ile Leu Ala Val Arg Arg
    50                  55                  60

Leu Gln Glu Glu Asp Gln Gln Phe Arg Thr Ser Ser Leu Pro Ala Ile
65                  70                  75                  80

Pro Asn Pro Phe Pro Glu Leu Cys Gly Pro Gly Ser Pro Val Leu
                85                  90                  95

Thr Pro Gly Ser Leu Pro Pro Ser Gln Ala Ala Lys Gln Asp Val
            100                 105                 110

Lys Val Phe Ser Glu Asp Gly Thr Ser Lys Val Val Glu Ile Leu Ala
        115                 120                 125

Asp Met Thr Ala Arg Asp Leu Cys Gln Leu Leu Val Tyr Lys Ser His
    130                 135                 140

Cys Val Asp Asp Asn Ser Trp Thr Leu Val Glu His His Pro His Leu
145                 150                 155                 160

Gly Leu Glu Arg Cys Leu Glu Asp His Glu Leu Val Val Gln Val Glu
                165                 170                 175

Ser Thr Met Ala Ser Glu Ser Lys Phe Leu Phe Arg Lys Asn Tyr Ala
```

```
                    180                 185                 190
Lys Tyr Glu Phe Phe Lys Asn Pro Met Asn Phe Phe Pro Glu Gln Met
            195                 200                 205
Val Thr Trp Cys Gln Gln Ser Asn Gly Ser Gln Thr Gln Leu Leu Gln
            210                 215                 220
Asn Phe Leu Asn Ser Ser Cys Pro Glu Ile Gln Gly Phe Leu His
225                 230                 235                 240
Val Lys Glu Leu Gly Lys Lys Ser Trp Lys Leu Tyr Val Cys Leu
                245                 250                 255
Arg Arg Ser Gly Leu Tyr Cys Ser Thr Lys Gly Thr Ser Lys Glu Pro
            260                 265                 270
Arg His Leu Gln Leu Leu Ala Asp Leu Glu Asp Ser Asn Ile Phe Ser
            275                 280                 285
Leu Ile Ala Gly Arg Lys Gln Tyr Asn Ala Pro Thr Asp His Gly Leu
            290                 295                 300
Cys Ile Lys Pro Asn Lys Val Arg Asn Glu Thr Lys Glu Leu Arg Leu
305                 310                 315                 320
Leu Cys Ala Glu Asp Glu Gln Thr Arg Thr Cys Trp Met Thr Ala Phe
                325                 330                 335
Arg Leu Leu Lys Tyr Glu Met Leu Leu Tyr Gln Asn Tyr Arg Ile Pro
            340                 345                 350
Gln Gln Arg Lys Ala Leu Leu Ser Pro Phe Ser Thr Pro Val Arg Ser
            355                 360                 365
Val Ser Glu Asn Ser Leu Val Ala Met Asp Phe Ser Gly Gln Thr Gly
            370                 375                 380
Arg Val Ile Glu Asn Pro Ala Glu Ala Gln Ser Ala Ala Leu Glu Glu
385                 390                 395                 400
Gly His Ala Trp Arg Lys Arg Ser Thr Arg Met Asn Ile Leu Gly Ser
                405                 410                 415
Gln Ser Pro Leu His Pro Ser Thr Leu Ser Thr Val Ile His Arg Thr
            420                 425                 430
Gln His Trp Phe His Gly Arg Phe Ser Arg Glu Glu Ser His Arg Ile
            435                 440                 445
Ile Lys Gln Gln Gly Leu Val Asp Gly Leu Phe Leu Leu Arg Asp Ser
450                 455                 460
Gln Ser Asn Pro Lys Ala Phe Val Leu Thr Leu Cys His His Gln Lys
465                 470                 475                 480
Ile Lys Asn Phe Gln Ile Leu Pro Cys Glu Asp Asp Gly Gln Thr Phe
                485                 490                 495
Phe Ser Leu Asp Asp Gly Asn Thr Lys Phe Ser Asp Leu Ile Gln Leu
            500                 505                 510
Val Asp Phe Tyr Gln Leu Asn Lys Gly Val Leu Pro Cys Lys Leu Lys
            515                 520                 525
His His Cys Ile Arg Val Ala Leu
            530                 535

<210> SEQ ID NO 6
<211> LENGTH: 1372
<212> TYPE: PRT
<213> ORGANISM: Mus musculus
<300> PUBLICATION INFORMATION:
<301> AUTHORS: Flores-Riveros, J R.
         Sibley, E
         Kastelic, T
         Lane, M D.
<302> TITLE: Substrate phosphorylation catalyzed by the insulin
``` receptor tyrosine kinase: Kinetic correlation to
autophosphorylation of specific sites in the beta
subunit
<303> JOURNAL: J. Biol. Chem.
<304> VOLUME: 264
<306> PAGES: 21557-21572
<307> DATE: 1989
<308> DATABASE ACCESSION NUMBER: J05149
<309> DATABASE ENTRY DATE: 1994-08-11

<400> SEQUENCE: 6

```
Met Gly Phe Gly Arg Gly Cys Glu Thr Thr Ala Val Pro Leu Leu Val
 1               5                  10                  15

Ala Val Ala Ala Leu Leu Val Gly Thr Ala Gly His Leu Tyr Pro Gly
             20                  25                  30

Glu Val Cys Pro Gly Met Asp Ile Arg Asn Asn Leu Thr Arg Leu His
         35                  40                  45

Glu Leu Glu Asn Cys Ser Val Ile Glu Gly His Leu Gln Ile Leu Leu
     50                  55                  60

Met Phe Lys Thr Arg Pro Glu Asp Phe Arg Asp Leu Ser Phe Pro Lys
 65                  70                  75                  80

Leu Ile Met Ile Thr Asp Tyr Leu Leu Leu Phe Arg Val Tyr Gly Leu
                 85                  90                  95

Glu Ser Leu Lys Asp Leu Phe Pro Asn Leu Thr Val Ile Arg Gly Ser
            100                 105                 110

Arg Leu Phe Phe Asn Tyr Ala Leu Val Ile Phe Glu Met Val His Leu
        115                 120                 125

Lys Glu Leu Gly Leu Tyr Asn Leu Met Asn Ile Thr Arg Gly Ser Val
    130                 135                 140

Arg Ile Glu Lys Asn Asn Glu Leu Cys Tyr Leu Ala Thr Ile Asp Trp
145                 150                 155                 160

Ser Arg Ile Leu Asp Ser Val Glu Asp Asn Tyr Ile Val Leu Asn Lys
                165                 170                 175

Asp Asp Asn Glu Glu Cys Gly Asp Val Cys Pro Gly Thr Ala Lys Gly
            180                 185                 190

Lys Thr Asn Cys Pro Ala Thr Val Ile Asn Gly Gln Phe Val Glu Arg
        195                 200                 205

Cys Trp Thr His Ser His Cys Gln Lys Val Cys Pro Thr Ile Cys Lys
    210                 215                 220

Ser His Gly Cys Thr Ala Glu Gly Leu Cys Cys His Lys Glu Cys Leu
225                 230                 235                 240

Gly Asn Cys Ser Glu Pro Asp Asp Pro Thr Lys Cys Val Ala Cys Arg
                245                 250                 255

Asn Phe Tyr Leu Asp Gly Gln Cys Val Glu Thr Cys Pro Pro Pro Tyr
            260                 265                 270

Tyr His Phe Gln Asp Trp Arg Cys Val Asn Phe Ser Phe Cys Gln Asp
        275                 280                 285

Leu His Phe Lys Cys Arg Asn Ser Arg Lys Pro Gly Cys His Gln Tyr
    290                 295                 300

Val Ile His Asn Asn Lys Cys Ile Pro Glu Cys Pro Ser Gly Tyr Thr
305                 310                 315                 320

Met Asn Ser Ser Asn Leu Met Cys Thr Pro Cys Leu Gly Pro Cys Pro
                325                 330                 335

Lys Val Cys Gln Ile Leu Glu Gly Glu Lys Thr Ile Asp Ser Val Thr
            340                 345                 350

Ser Ala Gln Glu Leu Arg Gly Cys Thr Val Ile Asn Gly Ser Leu Ile
```

-continued

```
             355                 360                 365
Ile Asn Ile Arg Gly Gly Asn Asn Leu Ala Ala Glu Leu Glu Ala Asn
        370                 375                 380
Leu Gly Leu Ile Glu Glu Ile Ser Gly Phe Leu Lys Ile Arg Arg Ser
385                 390                 395                 400
Tyr Ala Leu Val Ser Leu Ser Phe Phe Arg Lys Leu His Leu Ile Arg
                405                 410                 415
Gly Glu Thr Leu Glu Ile Gly Asn Tyr Ser Phe Tyr Ala Leu Asp Asn
                420                 425                 430
Gln Asn Leu Arg Gln Leu Trp Asp Trp Ser Lys His Asn Leu Thr Ile
            435                 440                 445
Thr Gln Gly Lys Leu Phe Phe His Tyr Asn Pro Lys Leu Cys Leu Ser
        450                 455                 460
Glu Ile His Lys Met Glu Glu Val Ser Gly Thr Lys Gly Arg Gln Glu
465                 470                 475                 480
Arg Asn Asp Ile Ala Leu Lys Thr Asn Gly Asp Gln Ala Ser Cys Glu
                485                 490                 495
Asn Glu Leu Leu Lys Phe Ser Phe Ile Arg Thr Ser Phe Asp Lys Ile
                500                 505                 510
Leu Leu Arg Trp Glu Pro Tyr Trp Pro Asp Phe Arg Asp Leu Leu
            515                 520                 525
Gly Phe Met Leu Phe Tyr Lys Glu Ala Pro Tyr Gln Asn Val Thr Glu
        530                 535                 540
Phe Asp Gly Gln Asp Ala Cys Gly Ser Asn Ser Trp Thr Val Val Asp
545                 550                 555                 560
Ile Asp Pro Pro Gln Arg Ser Asn Asp Pro Lys Ser Gln Thr Pro Ser
                565                 570                 575
His Pro Gly Trp Leu Met Arg Gly Leu Lys Pro Trp Thr Gln Tyr Ala
                580                 585                 590
Ile Phe Val Lys Thr Leu Val Thr Phe Ser Asp Glu Arg Arg Thr Tyr
            595                 600                 605
Gly Ala Lys Ser Asp Ile Ile Tyr Val Gln Thr Asp Ala Thr Asn Pro
        610                 615                 620
Ser Val Pro Leu Asp Pro Ile Ser Val Ser Asn Ser Ser Ser Gln Ile
625                 630                 635                 640
Ile Leu Lys Trp Lys Pro Pro Ser Asp Pro Asn Gly Asn Ile Thr His
                645                 650                 655
Tyr Leu Val Tyr Trp Glu Arg Gln Ala Glu Asp Ser Glu Leu Phe Glu
                660                 665                 670
Leu Asp Tyr Cys Leu Lys Gly Leu Lys Leu Pro Ser Arg Thr Trp Ser
            675                 680                 685
Pro Pro Phe Glu Ser Asp Asp Ser Gln Lys His Asn Gln Ser Glu Tyr
        690                 695                 700
Asp Asp Ser Ala Ser Glu Cys Cys Ser Cys Pro Lys Thr Asp Ser Gln
705                 710                 715                 720
Ile Leu Lys Glu Leu Glu Glu Ser Ser Phe Arg Lys Thr Phe Glu Asp
                725                 730                 735
Tyr Leu His Asn Val Val Phe Val Pro Arg Pro Ser Arg Lys Arg Arg
                740                 745                 750
Ser Leu Glu Glu Val Gly Asn Val Thr Ala Thr Thr Leu Thr Leu Pro
            755                 760                 765
Asp Phe Pro Asn Val Ser Ser Thr Ile Val Pro Thr Ser Gln Glu Glu
        770                 775                 780
```

-continued

```
His Arg Pro Phe Glu Lys Val Val Asn Lys Glu Ser Leu Val Ile Ser
785                 790                 795                 800

Gly Leu Arg His Phe Thr Gly Tyr Arg Ile Glu Leu Gln Ala Cys Asn
            805                 810                 815

Gln Asp Ser Pro Asp Glu Arg Cys Ser Val Ala Ala Tyr Val Ser Ala
            820                 825                 830

Arg Thr Met Pro Glu Ala Lys Ala Asp Asp Ile Val Gly Pro Val Thr
            835                 840                 845

His Glu Ile Phe Glu Asn Asn Val Val His Leu Met Trp Gln Glu Pro
            850                 855                 860

Lys Glu Pro Asn Gly Leu Ile Val Leu Tyr Glu Val Ser Tyr Arg Arg
865                 870                 875                 880

Tyr Gly Asp Glu Glu Leu His Leu Cys Val Ser Arg Lys His Phe Ala
                885                 890                 895

Leu Glu Arg Gly Cys Arg Leu Arg Gly Leu Ser Pro Gly Asn Tyr Ser
            900                 905                 910

Val Arg Val Arg Ala Thr Ser Leu Ala Gly Asn Gly Ser Trp Thr Glu
            915                 920                 925

Pro Thr Tyr Phe Tyr Val Thr Asp Tyr Leu Asp Val Pro Ser Asn Ile
930                 935                 940

Ala Lys Ile Ile Ile Gly Pro Leu Ile Phe Val Phe Leu Phe Ser Val
945                 950                 955                 960

Val Ile Gly Ser Ile Tyr Leu Phe Leu Arg Lys Arg Gln Pro Asp Gly
                965                 970                 975

Pro Met Gly Pro Leu Tyr Ala Ser Ser Asn Pro Glu Tyr Leu Ser Ala
            980                 985                 990

Ser Asp Val Phe Pro Ser Ser Val Tyr Val Pro Asp Glu Trp Glu Val
            995                 1000                1005

Pro Arg Glu Lys Ile Thr Leu Leu Arg Glu Leu Gly Gln Gly Ser Phe
            1010                1015                1020

Gly Met Val Tyr Glu Gly Asn Ala Lys Asp Ile Ile Lys Gly Glu Ala
1025                1030                1035                1040

Glu Thr Arg Val Ala Val Lys Thr Val Asn Glu Ser Ala Ser Leu Arg
            1045                1050                1055

Glu Arg Ile Glu Phe Leu Asn Glu Ala Ser Val Met Lys Gly Phe Thr
            1060                1065                1070

Cys His His Val Val Arg Leu Leu Gly Val Val Ser Lys Gly Gln Pro
            1075                1080                1085

Met Leu Val Val Met Glu Leu Met Ala His Gly Asp Leu Lys Ser His
            1090                1095                1100

Leu Arg Ser Leu Arg Pro Asp Ala Glu Asn Asn Pro Gly Arg Pro Pro
1105                1110                1115                1120

Pro Thr Leu Gln Glu Met Ile Gln Met Thr Ala Glu Ile Ala Asp Gly
            1125                1130                1135

Met Ala Tyr Leu Asn Ala Lys Lys Phe Val His Arg Asp Leu Ala Ala
            1140                1145                1150

Arg Asn Cys Met Val Ala His Asp Phe Thr Val Lys Ile Gly Asp Phe
            1155                1160                1165

Gly Met Thr Arg Asp Ile Tyr Glu Thr Asp Tyr Tyr Arg Lys Gly Gly
            1170                1175                1180

Lys Gly Leu Leu Pro Val Arg Trp Met Ser Pro Glu Ser Leu Lys Asp
1185                1190                1195                1200
```

-continued

```
Gly Val Phe Thr Ala Ser Ser Asp Met Trp Ser Phe Gly Val Val Leu
            1205                1210                1215

Trp Glu Ile Thr Ser Leu Ala Glu Gln Pro Tyr Gln Gly Leu Ser Asn
        1220                1225                1230

Glu Gln Val Leu Lys Phe Val Met Asp Gly Gly Tyr Leu Asp Pro Pro
        1235                1240                1245

Asp Asn Cys Pro Glu Arg Leu Thr Asp Leu Met Arg Met Cys Trp Gln
        1250                1255                1260

Phe Asn Pro Lys Met Arg Pro Thr Phe Leu Glu Ile Val Asn Leu Leu
1265                1270                1275                1280

Lys Asp Asp Leu His Pro Ser Phe Pro Glu Val Ser Phe Phe Tyr Ser
                1285                1290                1295

Glu Glu Asn Lys Ala Pro Glu Ser Glu Glu Leu Glu Met Glu Phe Glu
            1300                1305                1310

Asp Met Glu Asn Val Pro Leu Asp Arg Ser Ser His Cys Gln Arg Glu
            1315                1320                1325

Glu Ala Gly Gly Arg Glu Gly Gly Ser Ser Leu Ser Ile Lys Arg Thr
        1330                1335                1340

Tyr Asp Glu His Ile Pro Tyr Thr His Met Asn Gly Gly Lys Lys Asn
1345                1350                1355                1360

Gly Arg Val Leu Thr Leu Pro Arg Ser Asn Pro Ser
            1365                1370

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:F Linker
      Primer

<400> SEQUENCE: 7
tcgactcgag tatagttaca                                              20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:F Linker
      Primer

<400> SEQUENCE: 8
tgtaactata ctcgagt                                                 17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:A Linker
      Primer

<400> SEQUENCE: 9
gattactcga gactaatatc                                              20

<210> SEQ ID NO 10
<211> LENGTH: 17
<212> TYPE: DNA
<213> ORGANISM: Artificial Sequence
<220> FEATURE:
<223> OTHER INFORMATION: Description of Artificial Sequence:A Linker
```

```
                         Primer

<400> SEQUENCE: 10
gatattagtc tcgagta                                                    17

<210> SEQ ID NO 11
<211> LENGTH: 1877
<212> TYPE: DNA
<213> ORGANISM: Homo sapiens
<220> FEATURE:
<221> NAME/KEY: CDS
<222> LOCATION: (32)..(1816)

<400> SEQUENCE: 11
aaatgtaatt tgaagaaggc agaaggaacc c atg gct tta gcc ggc tgc cca        52
                                   Met Ala Leu Ala Gly Cys Pro
                                   1               5 gat tcc ttt ttg cac cat ccg tac tac cag gac aag gtg gag cag aca      100
Asp Ser Phe Leu His His Pro Tyr Tyr Gln Asp Lys Val Glu Gln Thr
            10                  15                  20 cct cgc agt caa caa gac ccg gca gga cca gga ctc ccc gca cag tct      148
Pro Arg Ser Gln Gln Asp Pro Ala Gly Pro Gly Leu Pro Ala Gln Ser
 25                  30                  35 gac cga ctt gcg aat cac cag gag gat gat gtg gac ctg gaa gcc ctg      196
Asp Arg Leu Ala Asn His Gln Glu Asp Asp Val Asp Leu Glu Ala Leu
 40                  45                  50                  55 gtg aac gat atg aat gca tcc ctg gag agc ctg tac tcg gcc tgc agc      244
Val Asn Asp Met Asn Ala Ser Leu Glu Ser Leu Tyr Ser Ala Cys Ser
                 60                  65                  70 atg cag tca gac acg gtg ccc ctc ctg cag aat ggc cag cat gcc cgc      292
Met Gln Ser Asp Thr Val Pro Leu Leu Gln Asn Gly Gln His Ala Arg
             75                  80                  85 agc cag cct cgg gct tca ggc cct cct cgg tcc atc cag cca cag gtg      340
Ser Gln Pro Arg Ala Ser Gly Pro Pro Arg Ser Ile Gln Pro Gln Val
         90                  95                 100 tcc ccg agg cag agg gtg cag cgc tcc cag cct gtg cac atc ctc gct      388
Ser Pro Arg Gln Arg Val Gln Arg Ser Gln Pro Val His Ile Leu Ala
     105                 110                 115 gtc agg cgc ctt cag gag gaa gac cag cag ttt aga acc tca tct ctg      436
Val Arg Arg Leu Gln Glu Glu Asp Gln Gln Phe Arg Thr Ser Ser Leu
120                 125                 130                 135 ccg gcc atc ccc aat cct ttt cct gaa ctc tgt ggc cct ggg agc ccc      484
Pro Ala Ile Pro Asn Pro Phe Pro Glu Leu Cys Gly Pro Gly Ser Pro
                140                 145                 150 cct gtg ctc acg ccg ggt tct tta cct ccg agc cag gcc gcc gca aag      532
Pro Val Leu Thr Pro Gly Ser Leu Pro Pro Ser Gln Ala Ala Ala Lys
            155                 160                 165 cag gat gtt aaa gtc ttt agt gaa gat ggg aca agc aaa gtg gtg gag      580
Gln Asp Val Lys Val Phe Ser Glu Asp Gly Thr Ser Lys Val Val Glu
        170                 175                 180 att cta gca gac atg aca gcc aga gac ctg tgc caa ttg ctg gtt tac      628
Ile Leu Ala Asp Met Thr Ala Arg Asp Leu Cys Gln Leu Leu Val Tyr
    185                 190                 195 aaa agt cac tgt gtg gat gac aac agc tgg aca cta gtg gag cac cac      676
Lys Ser His Cys Val Asp Asp Asn Ser Trp Thr Leu Val Glu His His
200                 205                 210                 215 ccg cac cta gga tta gag agg tgc ttg gaa gac cat gag ctg gtg gtc      724
Pro His Leu Gly Leu Glu Arg Cys Leu Glu Asp His Glu Leu Val Val
                220                 225                 230 cag gtg gag agt acc atg gcc agt gag agt aaa ttt cta ttc agg aag      772
Gln Val Glu Ser Thr Met Ala Ser Glu Ser Lys Phe Leu Phe Arg Lys
```

```
                235                 240                 245
aat tac gca aaa tac gag ttc ttt aaa aat ccc atg aat ttc ttc cca    820
Asn Tyr Ala Lys Tyr Glu Phe Phe Lys Asn Pro Met Asn Phe Phe Pro
        250                 255                 260 gaa cag atg gtt act tgg tgc cag cag tca aat ggc agt caa acc cag    868
Glu Gln Met Val Thr Trp Cys Gln Gln Ser Asn Gly Ser Gln Thr Gln
265                 270                 275 ctt ttg cag aat ttt ctg aac tcc agt agt tgt cct gaa att caa ggg    916
Leu Leu Gln Asn Phe Leu Asn Ser Ser Ser Cys Pro Glu Ile Gln Gly
280                 285                 290                 295 ttt ttg cat gtg aaa gag ctg gga aag aaa tca tgg aaa aag ctg tat    964
Phe Leu His Val Lys Glu Leu Gly Lys Lys Ser Trp Lys Lys Leu Tyr
                300                 305                 310 gtg tgt ttg cgg aga tct ggc ctt tat tgc tcc acc aag gga act tca   1012
Val Cys Leu Arg Arg Ser Gly Leu Tyr Cys Ser Thr Lys Gly Thr Ser
            315                 320                 325 aag gaa ccc aga cac ctg cag ctg ctg gcc gac ctg gag gac agc aac   1060
Lys Glu Pro Arg His Leu Gln Leu Leu Ala Asp Leu Glu Asp Ser Asn
        330                 335                 340 atc ttc tcc ctg atc gct ggc agg aag cag tac aac gcc cct aca gac   1108
Ile Phe Ser Leu Ile Ala Gly Arg Lys Gln Tyr Asn Ala Pro Thr Asp
    345                 350                 355 cac ggg ctc tgc ata aag cca aac aaa gtc agg aat gaa act aaa gag   1156
His Gly Leu Cys Ile Lys Pro Asn Lys Val Arg Asn Glu Thr Lys Glu
360                 365                 370                 375 ctg agg ttg ctc tgt gca gag gac gag caa acc agg acg tgc tgg atg   1204
Leu Arg Leu Leu Cys Ala Glu Asp Glu Gln Thr Arg Thr Cys Trp Met
                380                 385                 390 aca gcg ttc aga ctc ctc aag tat gga atg ctc ctt tac cag aat tac   1252
Thr Ala Phe Arg Leu Leu Lys Tyr Gly Met Leu Leu Tyr Gln Asn Tyr
            395                 400                 405 cga atc cct cag cag agg aag gcc ttg ctg tcc ccg ttc tcg acg cca   1300
Arg Ile Pro Gln Gln Arg Lys Ala Leu Leu Ser Pro Phe Ser Thr Pro
        410                 415                 420 gtg cgc agt gtc tcc gag aac tcc ctc gtg gca atg gat ttt tct ggg   1348
Val Arg Ser Val Ser Glu Asn Ser Leu Val Ala Met Asp Phe Ser Gly
    425                 430                 435 caa aca gga cgc gtg ata gag aat ccg gcg gag gcc cag agc gca gcc   1396
Gln Thr Gly Arg Val Ile Glu Asn Pro Ala Glu Ala Gln Ser Ala Ala
440                 445                 450                 455 ctg gag gag ggc cac gcc tgg agg aag cga agc aca cgg atg aac atc   1444
Leu Glu Glu Gly His Ala Trp Arg Lys Arg Ser Thr Arg Met Asn Ile
                460                 465                 470 cta ggt agc caa agt ccc ctc cac cct tct acc cta agt aca gtg att   1492
Leu Gly Ser Gln Ser Pro Leu His Pro Ser Thr Leu Ser Thr Val Ile
            475                 480                 485 cac agg aca cag cac tgg ttt cac ggg agg atc tcc agg gag gaa tcc   1540
His Arg Thr Gln His Trp Phe His Gly Arg Ile Ser Arg Glu Glu Ser
        490                 495                 500 cac agg atc att aaa cag caa ggg ctc gtg gat ggg ctt ttt ctc ctc   1588
His Arg Ile Ile Lys Gln Gln Gly Leu Val Asp Gly Leu Phe Leu Leu
    505                 510                 515 cgt gac agc cag agt aat cca aag gca ttt gta ctc aca ctg tgt cat   1636
Arg Asp Ser Gln Ser Asn Pro Lys Ala Phe Val Leu Thr Leu Cys His
520                 525                 530                 535 cac cag aaa att aaa aat ttc cag atc tta cct tgc gag gac gac ggg   1684
His Gln Lys Ile Lys Asn Phe Gln Ile Leu Pro Cys Glu Asp Asp Gly
                540                 545                 550 cag acg ttc ttc agc cta gat gac ggg aac acc aaa ttc tct gac ctg   1732
Gln Thr Phe Phe Ser Leu Asp Asp Gly Asn Thr Lys Phe Ser Asp Leu
```

-continued

```
Gln Thr Phe Phe Ser Leu Asp Asp Gly Asn Thr Lys Phe Ser Asp Leu
            555                 560                 565 atc cag ctg gtt gac ttt tac cag ctg aac aaa gga gtc ctg cct tgc      1780
Ile Gln Leu Val Asp Phe Tyr Gln Leu Asn Lys Gly Val Leu Pro Cys
            570                 575                 580 aaa ctc aag cac cac tgc atc cga gtg gcc tta tga ccgcagatgt           1826
Lys Leu Lys His His Cys Ile Arg Val Ala Leu
585                 590                 595 cctctcggct gaagactgga ggaagtgaac actggagtga agaagcggtc t             1877
```

<210> SEQ ID NO 12
<211> LENGTH: 594
<212> TYPE: PRT
<213> ORGANISM: Homo sapiens

<400> SEQUENCE: 12

```
Met Ala Leu Ala Gly Cys Pro Asp Ser Phe Leu His His Pro Tyr Tyr
1               5                   10                  15

Gln Asp Lys Val Glu Gln Thr Pro Arg Ser Gln Gln Asp Pro Ala Gly
            20                  25                  30

Pro Gly Leu Pro Ala Gln Ser Asp Arg Leu Ala Asn His Gln Glu Asp
        35                  40                  45

Asp Val Asp Leu Glu Ala Leu Val Asn Asp Met Asn Ala Ser Leu Glu
    50                  55                  60

Ser Leu Tyr Ser Ala Cys Ser Met Gln Ser Asp Thr Val Pro Leu Leu
65                  70                  75                  80

Gln Asn Gly Gln His Ala Arg Ser Gln Pro Arg Ala Ser Gly Pro Pro
                85                  90                  95

Arg Ser Ile Gln Pro Gln Val Ser Pro Arg Gln Arg Val Gln Arg Ser
            100                 105                 110

Gln Pro Val His Ile Leu Ala Val Arg Arg Leu Gln Glu Glu Asp Gln
        115                 120                 125

Gln Phe Arg Thr Ser Ser Leu Pro Ala Ile Pro Asn Pro Phe Pro Glu
    130                 135                 140

Leu Cys Gly Pro Gly Ser Pro Pro Val Leu Thr Pro Gly Ser Leu Pro
145                 150                 155                 160

Pro Ser Gln Ala Ala Lys Gln Asp Val Lys Val Phe Ser Glu Asp
                165                 170                 175

Gly Thr Ser Lys Val Val Glu Ile Leu Ala Asp Met Thr Ala Arg Asp
            180                 185                 190

Leu Cys Gln Leu Leu Val Tyr Lys Ser His Cys Val Asp Asp Asn Ser
        195                 200                 205

Trp Thr Leu Val Glu His His Pro His Leu Gly Leu Glu Arg Cys Leu
    210                 215                 220

Glu Asp His Glu Leu Val Val Gln Val Glu Ser Thr Met Ala Ser Glu
225                 230                 235                 240

Ser Lys Phe Leu Phe Arg Lys Asn Tyr Ala Lys Tyr Glu Phe Phe Lys
                245                 250                 255

Asn Pro Met Asn Phe Phe Pro Glu Gln Met Val Thr Trp Cys Gln Gln
            260                 265                 270

Ser Asn Gly Ser Gln Thr Gln Leu Leu Gln Asn Phe Leu Asn Ser Ser
        275                 280                 285

Ser Cys Pro Glu Ile Gln Gly Phe Leu His Val Lys Glu Leu Gly Lys
    290                 295                 300

Lys Ser Trp Lys Lys Leu Tyr Val Cys Leu Arg Arg Ser Gly Leu Tyr
```

-continued

```
305                 310                 315                 320
Cys Ser Thr Lys Gly Thr Ser Lys Glu Pro Arg His Leu Gln Leu Leu
                325                 330                 335

Ala Asp Leu Glu Asp Ser Asn Ile Phe Ser Leu Ile Ala Gly Arg Lys
                340                 345                 350

Gln Tyr Asn Ala Pro Thr Asp His Gly Leu Cys Ile Lys Pro Asn Lys
                355                 360                 365

Val Arg Asn Glu Thr Lys Glu Leu Arg Leu Leu Cys Ala Glu Asp Glu
    370                 375                 380

Gln Thr Arg Thr Cys Trp Met Thr Ala Phe Arg Leu Leu Lys Tyr Gly
385                 390                 395                 400

Met Leu Leu Tyr Gln Asn Tyr Arg Ile Pro Gln Gln Arg Lys Ala Leu
                405                 410                 415

Leu Ser Pro Phe Ser Thr Pro Val Arg Ser Val Ser Glu Asn Ser Leu
                420                 425                 430

Val Ala Met Asp Phe Ser Gly Gln Thr Gly Arg Val Ile Glu Asn Pro
                435                 440                 445

Ala Glu Ala Gln Ser Ala Ala Leu Glu Glu Gly His Ala Trp Arg Lys
    450                 455                 460

Arg Ser Thr Arg Met Asn Ile Leu Gly Ser Gln Ser Pro Leu His Pro
465                 470                 475                 480

Ser Thr Leu Ser Thr Val Ile His Arg Thr Gln His Trp Phe His Gly
                485                 490                 495

Arg Ile Ser Arg Glu Glu Ser His Arg Ile Ile Lys Gln Gln Gly Leu
                500                 505                 510

Val Asp Gly Leu Phe Leu Leu Arg Asp Ser Gln Ser Asn Pro Lys Ala
                515                 520                 525

Phe Val Leu Thr Leu Cys His His Gln Lys Ile Lys Asn Phe Gln Ile
                530                 535                 540

Leu Pro Cys Glu Asp Asp Gly Gln Thr Phe Phe Ser Leu Asp Asp Gly
545                 550                 555                 560

Asn Thr Lys Phe Ser Asp Leu Ile Gln Leu Val Asp Phe Tyr Gln Leu
                565                 570                 575

Asn Lys Gly Val Leu Pro Cys Lys Leu Lys His His Cys Ile Arg Val
                580                 585                 590

Ala Leu
```

MAMMALIAN MODEL FOR DIABETES

This application is a Continuation-in-part of U.S. application Ser. No. 10/111,183, filed Aug. 18, 2000, which is herein incorporated by reference in the entirety.

TECHNICAL FIELD

This invention relates to a non-human model mammal for diabetes onset, such as a diabetic-prone transgenic mouse, and to a screening method of a remedy for diabetes using the same.

BACKGROUND ART

Diabetes, which is comprised of various disorders of metabolism, mainly that of carbohydrate metabolism caused by relative or absolute lack of insulin activity, is roughly classified into two types. One is insulin-dependent diabetes mellitus (type I: IDDM), and the other is noninsulin-dependent diabetes mellitus (type II: NIDDM). The onset of insulin-dependent diabetes mellitus is brought by hyposecretion of insulin as a result of the progressive disruption of β cells in pancreatic islet caused by an auto-immune mechanism. On the other hand, the onset of noninsulin-dependent diabetes mellitus is triggered when insulin resistance caused by obesity is added to diatheses of inherited hyposecretion of insulin and insulin resistance in skeletal muscles. This noninsulin-dependent diabetes mellitus makes up 95% or more of whole diabetes.

So far, examples of diabetes where its cause is elucidated at a gene level include insulin abnormality, insulin receptor abnormality, glucokinase gene abnormality (MODY2) and diabetes caused by abnormality of mitochondrial DNA. In addition, locations of MODY1, MODY3, NIDDM1 and NIDDM2 genes on a chromosome have been mapped by linkage analysis. Meanwhile, a NOD (non-obese diabetic) mouse, diabetes-inducing transgenic mouse being introduced with diabetogenic gene wherein a human insulin gene promoter is fused with a thermal shock protein 70 gene attached to a lower part of the promoter (Japanese Laid-Open Patent Application No. 9-28384), a transgenic fish having a humanized insulin gene being modified to secrete human insulin (Published Japanese Translation of PCT International Publication No. 10-504725), and a transgenic animal model for type II diabetes mellitus (Published Japanese Translation of PCT International Publication No. 10-507084) have been proposed as model animals for diabetes.

On the other hand, it has been found that genome imprinting is a gene expression mode only observed in mammals as far as higher vetebrates are concerned, and plays a crucial role in ontogeny, growth, behavior and the like of mammals, and affects a certain kind of gene disease and oncogenesis in human being. This genome imprinting is known as a phenomenon where paternal and maternal genomes play functionally different roles in ontogeny (Cell 45, 127, 1986, Cell 37, 179, 1984, Nature 315, 496, 1985).

The above-mentioned genome imprinted gene has been found in 1991 at the first time (Cell 64, 849, 1991), revealing that there are gene populations that exhibit paternal and maternal expressions, and it has been already reported that more than 30 genes of this type are present in a human and a mouse. Further, understanding of the molecular mechanism of genome imprinting that affects ontogeny, growth and behavior of mammals makes it possible to elucidate direct or indirect causes of fetal death, neonatal death, overgrowth, growth retardation, behavioral disturbance [Nature 315, 496, 1985, Frontiers in Molecular Biology, p 118, (IRL Press, Oxford, 1997)] induced by overexpression or lack of expression of a specific imprinted gene (population) and some human hereditary diseases (Trends Genet 5, 331, 1989, Semin Cancer Biol 3, 151, 1992, Hum Mol Genet 4, 1757, 1995, Trends Genet 13, 436, 1997).

Conventionally known separating methods of such genome imprinted gene include a method utilizing sexual differences in metylation level in genomic DNA (RLGS; restriction landmark genomic scanning), and a method utilizing the difference in gene (cDNA) expression from male and female genomes (differential display method, allelic message display method, unichromosomal transfer method, and subtraction-hybridization method). The subtraction-hybridization method, which is developed by the inventors, is a separating method of Peg (a gene population expressed only from paternal genomes) and Meg (a gene population expressed only from maternal genomes) that utilizes the difference in gene expression between a parthenogenetic embryo having maternal genomes only or an androgenetic embryo having paternal genomes only and a normal fertilized embryo. By the subtraction-hybridization method, the inventors have separated a Meg 1 gene and determined the base sequence of this imprinted Meg 1 gene, and already elucidated that the gene is functionally identical to the known Grb10 gene (Oncogene 10, 1621-1630, 1995) (Proc. Natl. Acad. Sci. USA. 95, 1102-1107, 1998).

After insulin and insulin-like growth factor (IGF) bind to an insulin receptor and an IGF1 receptor respectively, tyrosin residues of these receptors are phosphorylated, and cell proliferation and carbohydrate metabolism are adjusted by transmitting this phosphorylation to downstream proteins (IRS-1 to IRS-4, etc). An object of the present invention is to provide a model mammal for diabetes onset being useful for the elucidation of an onset mechanism of diabetes caused by a blockage of signal transduction from insulin, and for the development of a remedy for said diabetes, and to provide a screening method of a remedy for said diabetes, and the like.

DISCLOSURE OF THE INVENTION

The inventors of the present invention have constructed a transgenic mouse by a process comprising the steps of: a transgene is prepared by incorporating a Meg1/Grb10 gene, which have been separated by a screening of an imprinted gene that exhibits maternal expression, into a vector; the transgene is microinjected into a male pronucleus of a fertilized egg and is cultured; subsequently the transgene is brought back into an oviduct of a pseudopregnant mouse, and the inventors have found that the diabetes onset is triggered by the overexpression of a Meg1/Grb10 gene in the transgenic mouse, and thus the present invention has completed.

The present invention relates to a transgenic non-human mammal into which a Meg1/Grb10 gene is introduced, the transgenic non-human mammal wherein the Meg1/Grb10 gene encodes a protein comprising an amino acid sequence described in Seq. ID No. 2 in a sequence listing, the transgenic non-human mammal as described above, wherein the gene that encodes the protein comprising the amino acid sequence described in Seq. ID No. 2 in the sequence listing is a mouse Meg1/Grb10 gene comprising a DNA sequence described in Seq. ID No. 1 in the sequence listing, the transgenic non-human mammal as described above, wherein a transgene containing a chicken β-actin promoter, a Meg1/

Grb10 gene and a rabbit β-globin poly A signal, which are sequenced in this order, is used as the Meg1/Grb10 gene, the transgenic non-human mammal as described above, wherein the transgene containing a chicken β-actin promoter, a Meg1/Grb10 gene and a rabbit β-globin poly A signal, which are sequenced in this order, as the Meg1/Grb10 gene, is a DNA sequence described in Seq. ID No. 3 in the sequence listing, a transgenic non-human mammal into which a human GRB10 gene is introduced, the transgenic non-human mammal into which a human GRB10 gene is introduced, wherein a transgene containing a chicken β-actin promoter, a human GRB10 gene and a rabbit β-globin poly A signal, which are sequenced in this order, is used as the human GRB10 gene, the transgenic non-human mammal according to any of the above, wherein the transgenic non-human mammal is diabetic-prone, and the transgenic non-human mammal according to any of the above, wherein the non-human mammal is a mouse.

The present invention also relates to a generating method of a transgenic mouse characterized in comprising the steps of: a transgene containing cDNA that encodes a Meg1/Grb10 protein in the downstream of a chicken β-actin promoter and in the upstream of a rabbit β-globin poly A is constructed, and subsequently the transgene is microinjected into a male proneucleus of a mouse fertilized egg; thus obtained egg cell is cultured and then transplanted into an oviduct of a pseudopregnant female mouse; after rearing up the recipient animal, baby mice that have the above-mentioned cDNA are selected from the mice born from the recipient animal, the generating method of a transgenic mouse, wherein the Meg1/Grb10 protein comprises an amino acid sequence described in Seq. ID No. 2 in the sequence listing, the generating method of a transgenic mouse wherein the Meg1/Grb10 protein comprises an amino acid sequence described in Seq. ID No. 2, wherein the transgene comprises a DNA sequence described in Seq. ID No. 3 in the sequence listing, and a generating method of a transgenic mouse characterized in comprising the steps of: a transgene containing cDNA that encodes a human GRB10 protein in the downstream of a chicken β-actin promoter and in the upstream of a rabbit β-globin poly A is constructed, and subsequently the transgene is microinjected into a male proneucleus of a mouse fertilized egg; thus obtained egg cell is cultured and then transplanted into an oviduct of a pseudopregnant female mouse; after rearing up the recipient animal, baby mice that have the above-mentioned cDNA are selected from the mice born from the recipient animal.

The present invention further relates to a screening method of a remedy for diabetes characterized in using a Meg1/Grb10 gene, a screening method of a remedy for diabetes characterized in using a human GRB10 gene, the screening method of a remedy for diabetes, wherein the transgenic non-human mammal as described hereinabove is used, the screening method of a remedy for diabetes, wherein a subject material is administered to a transgenic non-human mammal and the level of glucose in urine and/or blood obtained from the transgenic non-human mammal is measured, the screening method of a remedy for diabetes wherein the transgenic non-human mammal is a mouse, the screening method of a remedy for diabetes wherein a cell into which a Meg1/Grb10 gene and a subject material are introduced is cultured, and the Meg1/Grb10 gene is expressed in the cultured cell, and then the activity of a Meg1/Grb10 protein is measured, the screening method of a remedy for diabetes using the Meg1/Grb10 gene, wherein the expression of the Meg1/Grb10 gene is a stable expression the screening method of a remedy for diabetes wherein a cell into which a human GRB10 gene and a subject material are introduced is cultured, and the human GRB10 gene is expressed in the cultured cell, and then the activity of a human GRB10 protein is measured, the screening method of a remedy for diabetes wherein the expression of the human GRB10 gene is a stable expression, the screening method of a remedy for diabetes using a meg1/Grb10 gene and a subject material, wherein the subject material is a protein, and the subject material is introduced into a cell as DNA that encodes the protein, the screening method of a remedy for diabetes using a Meg1/Grb10 gene and a subject material, wherein the cell is derived from a human, a screening method of a remedy for diabetes characterized by that a Meg1/Grb10 protein and a subject material are brought into contact with each other in liquid phase and the activity of the Meg1/Grb10 protein is measured, a screening method of a remedy for diabetes characterized by that a human GRB10 protein and a subject material are brought into contact with each other in liquid phase and the activity of the human GRB10 protein is measured, and a remedy for diabetes obtained by the screening method of a remedy for diabetes according to any of the above.

BEST MODE FOR CARRYING OUT THE INVENTION

Figure 1:
FIG. 1 is a view showing an F-linker represented by SEQ ID NO: 7 used in the present invention and the complementary 17 mer sequence represented by SEQ ID NO:8.

In the present invention, a Meg1/Grb10 gene includes a Meg1 gene and a Grb10 gene of mammals, and further, a mutant gene and the like having a same function as said genes. Here, a Grb10 gene means a gene that encodes a growth factor receptor bound protein 10, a negative regulating factor in information pathway of insulin and/or insulin-like growth factor (IGF), and specific examples of the Grb10 gene have been reported by Ooi et al. as previously described (Oncogene 10, 1621-1630, 1995). A Meg1 gene means a gene which can be separated by subtraction-hybridization method that utilizes the difference in gene expressions between an androgenetic embryo and a normal fertilized embryo, and which has a same function as that of said Grb10 gene. The present inventors have reported that a mouse Meg1 gene is a splicing mutant of a mouse Grb10 gene (Proc. Natl. Acad. Sci. USA. 95, 1102-1107, 1998).

As a Meg1/Grb10 gene of the present invention, any gene can be used as long as it is a gene of a non-human mammal such as a rat, a rabbit or the like and is homologous to a mouse Meg1/Grb10 gene. For example, a gene that encodes a protein comprising an amino acid sequence described in Seq. ID No. 2 in the sequence listing, in particular, a mouse Meg1/Grb10 gene comprising a DNA sequence described in Seq. ID No. 1 in the sequence listing can be specifically exemplified. Further, as a human GRB10 gene of the present invention, a gene that encodes a protein comprising an amino acid sequence described in Seq. ID No. 5 or 12 in the sequence listing, in particular, a human GRB10 gene comprising a DNA sequence described in Seq. ID No. 4 or 11 in the sequence listing can be specifically exemplified. A human GRB10 gene is located on a human chromosome 7q11.2-12 (Genomics 40, 215-216, 1997), and is known as a candidate gene for Silver-Russell syndrome. The human GRB10 gene can be isolated by a usual method utilizing its homology to said mouse Meg1/Grb10 gene cDNA.

Examples of a transgene of the present invention include a transgene wherein said Meg1/Grb10 gene or said human GRB10 gene is constructed as a recombinant gene bound to the downstream of an appropriate promoter for mammals, and to the upstream of poly A signal. However, the kind of said promoter for mammals and poly A signal is not limited particularly. In addition, a transgene having an enhancer or a terminator may also be used. As the transgene, for instance, a transgene that contains a chicken β-actin promoter, said Meg1/Grb10 gene or said human GRB10 gene, and a rabbit β-globin poly A signal, which are sequenced in this order, in particular, a transgene which comprises a DNA sequence described in Seq. ID No. 3 in the sequence listing are specifically exemplified.

When a Meg1/Grb10 gene or a human GRB10 gene being incorporated into said transgene is expressed in a cell such as a fertilized egg, a Meg1/Grb10 protein or a human GRB10 protein is produced in the cell. The amino acid sequence of a mouse Meg1 protein is described in Seq. ID No. 2 in the sequence listing as aforementioned. Further, the amino acid sequence of known human GRB10 protein is also described in Seq. ID No. 5 or 12 in the sequence listing as aforementioned.

The transgenic non-human mammals of the present invention can be generated by a process comprising the steps of: a Meg1/Grb10 gene or a human GRB10 gene is introduced into a fertilized egg of a non-human mammal such as a mouse; the fertilized egg is transplanted into a pseudopregnant female non-human mammal; the non-human mammal is delivered of a non-human mammal introduced with a Meg1/Grb10 gene or a human GRB10 gene. As the non-human mammal, mammals such as a mouse, a rat, a rabbit and the like are exemplified, but a mouse is preferable in view of easiness in its generation, raising, use and the like. The method of introducing a gene into a fertilized egg is not limited in particular, and microinjection, electroporation and other such methods are exemplified as examples.

With a transgenic mouse as an example of the transgenic non-human mammal, the generating method of a transgenic mouse is explained more specifically as follows: a transgene containing cDNA that encodes an expression product of a Meg1/Grb10 gene or a human GRB10 gene in the downstream of a chicken β-actin promoter and in the upstream of a rabbit β-globin poly A is constructed, and subsequently the transgene is microinjected into a male proneucleus of a mouse fertilized egg; thus obtained egg cell is cultured and then transplanted into an oviduct of a pseudopregnant female mouse; after rearing up the recipient animal, baby mice that have the above-mentioned cDNA are selected from the mice born from the recipient animal. As the above-mentioned fertilized egg of a mouse, any fertilized egg obtained through a mating of mice derived from 129/sv, C57BL/6, BALB/c, C3H, SJL/Wt or the like can be used, however, it is preferable to use a fertilized egg from B6C3H mice being obtainable by mating a C57BL/6 (B6) mouse with a C3H mouse because it is possible to distinguish the independence of male and female pronuclei in cytoplasm at a pronuclear stage. Further, the appropriate number of transgenes to be introduced is 100 to 3000 molecules per fertilized egg. Still further, the baby mice having cDNA can be selected by dot hybridization method wherein a Meg1/Grb10 gene or a human GRB10 gene being introduced with crude DNA extracted from a tail of a mouse or the like is used as a probe, PCR method using a specific primer, or other such methods.

The screening method of a remedy for diabetes of the present invention is characterized in using a Meg1/Grb10 gene or a human GRB10 gene. The Meg1/Grb10 gene, in particular, is revealed to be an imprinted gene as aforementioned, and exhibits single-parental expression in its normal state, and when it exhibits overexpression or lack of expression, various influences are observed. The transgenic non-human mammals of the present invention into which a Meg1/Grb10 gene, a maternal imprinted gene, is introduced exhibit the overexpression of the gene. Among them, only male mice that inherit this gene develop diabetes, while female mice show extremely low incidence of diabetes, or extremely mild symptom. Therefore, in the screening method of a remedy for diabetes of the present invention, the male transgenic non-human mammals of the present invention are usually used, but the female transgenic mammals may also be used as littermate controls for the screening of a remedy for diabetes, or used for elucidating the onset mechanism of diabetes caused by the blockage of signal transmitting from insulin.

For the screening method of a remedy for diabetes of the present invention using the transgenic non-human mammal of the present invention, a diabetic-prone transgenic non-human mammal is mainly used. Specifically, by administering a subject material to a diabetic-prone transgenic non-human mammal, for example, a male transgenic mouse, and then by measuring the glucose level in urine, or blood collected from the foot of an eye ball, a tail or the like, of the transgenic non-human mammal, or by considering the survival rate etc, the therapeutic effect of the subject material against diabetes is evaluated.

As the screening method of a remedy for diabetes of the present invention using a Meg1/Grb10 gene or a human GRB10 gene, in addition to the above-stated in vivo screening method using the transgenic non-human mammal of the present invention, an in vitro screening method is exemplified. An example of the in vitro screening method of a remedy for diabetes of the present invention includes a screening method comprising the steps of: a Meg1/Grb10 gene or a human GRB10 gene and a subject material are introduced into a cell and the cell is cultured; the Meg1/Grb10 gene or the human GRB10 gene is expressed in the cultured cell; the activity of a Meg1/Grb10 protein or a human GRB10 protein is measured. For example, there is a method wherein a screening is conducted by comparing to controls into which no subject material is introduced, using the activity of the Meg1/Grb10 protein or the human GRB10 protein as an index.

In order to introduce a Meg1/Grb10 gene or a human GRB10 gene into a cell, known DNA introducing methods can be used. For example, there are method wherein the gene is incorporated into an expression vector or the like having a retrovirus LTR promoter, an adenovirus major late promoter or the like to be transfected, and a method wherein said transgene is microinjected. However, an introducing method that can construct a stable expression system, such as transfection or the like, is preferable because stable expression is more desirable than transient expression with regard to the intracellular expression of the gene. On the other hand, an example of a method for introducing a subject material into a cell includes a method wherein a solution containing the subject material is microinjected. Further, when a protein is used as the subject material, DNA that encodes the protein can be incorporated into a vector or the like to be transfected.

As a cell into which a Meg1/Grb10 gene or a human GRB10 gene, and/or a subject material are introduced, any cell can be used as long as it can express a Meg1/Grb10 gene or a human GRB10 gene. Examples of a cell that expresses a Meg1/Grb10 gene or a human GRB10 gene include BHK21 (ATCC CCL-10), CHO (ATCC CCL-61), HeLa (ATCC CCL-2), COS (ATCC CRL-1650); human cells derived from human pancreas such as Capan-1 (ATCC HTB-79), Capan-2 (ATCC HTB-80), COLO 587 (ATCC CRL-2000), HPAF-II (ATCC CRL-1997), Hs 766T (ATCC HTB-134); and human cells derived from human lymphocytes such as DAKIKI (ATCC TIB-206), C5/MJ (ATCC CRL-8293).

An example of the in vitro screening method of a remedy for diabetes of the present invention includes a screening method comprising the steps of: a Meg1/Grb10 protein or a human GRB10 protein and a subject material are brought into contact with each other in liquid phase, for instance, in buffer liquid; the activity of the Meg1/Grb10 protein or the human GRB10 protein is measured. As a measuring method of the activity of a Meg1/Grb10 protein or a human GRB10 protein, any method can be used as long as it utilizes the action/function of the Meg1/Grb10 protein or the human GRB10 protein. For example, there is a method for detecting the inhibition level of the binding between said protein and an insulin receptor. More specifically, a method wherein a radioactive substance or a whole or SH2 domain (region from the $568^{th}$ position to the $596^{th}$ position in an amino acid sequence described in Seq. ID No. 2 in the sequence listing) of a fluorescence-labeled Meg1/Grb10 protein and a subject material are brought into contact with cytoplasm (region from the $968^{th}$ position to the $1372^{th}$ position in an amino acid sequence described in Seq. ID No. 6 in the sequence listing) of an insulin receptor, and then precipitation is carried out with an antibody to the insulin receptor (immune antibody precipitation method), a surface plasmon resonance biosensor method comprising the steps of: the cytoplasm of the insulin receptor is bound onto a sensor chip; the sensor chip is soaked in a solution containing a subject material and a whole or SH2 domain of a Meg1/Grb10 protein; the number of bound molecules is detected, or other such methods can be exemplified.

Hereinafter, the present invention is explained in detail with reference to examples, however, the technical scope of the present invention is not limited to the examples.

EXAMPLE 1 [PREPARATION OF A MEG1/GRB10 GENE]

(Isolation of Androgenetic and Normal Fertilized Embryos)

By pronuclear transplantation according to the method previously described (Manipulations of Genetic Constitution by Nuclear Transplantation, Vol. 225, 732-744, 1993), an unfertilized egg was artificially developed so that it had genomes derived only from its mother of 129/sv strain, with the result that an androgenetic embryo (an early embryo of a mouse; day 9.5) was generated, and thus generated androgenetic embryo was then isolated. A normal fertilized embryo having genomes derived from both its father (sperm) and mother (ovum) of 129/sv strain was isolated by a usual method.

(Construction of cDNA Library)

Figure 2:
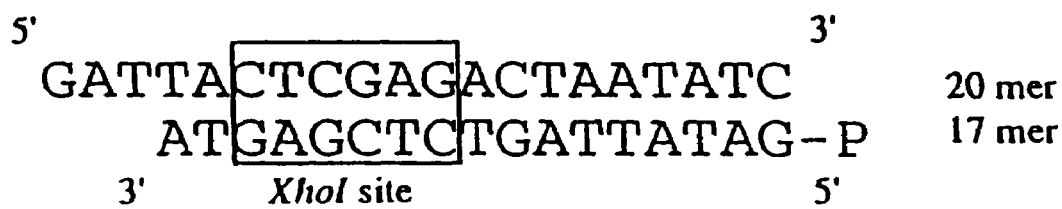
FIG. 2 is a view showing an A-linker represented by SEQ ID NO: 9 used in the present invention and the complementary 17 mer sequence represented by SEQ ID NO:10.

By an oligo (dT)-cellulose method using the micro FAST TRACK (Invitrogen), mRNA was purified from each of the normal fertilized embryo and the androgenetic embryo, then added with glycogen and precipitated by ethanol precipitation to be collected. Next, in order to synthesize cDNA, 500 ng each of said collected mRNA was subjected to reverse transcription according to the instructions provided in the λZAPII cDNA synthesis kit (Stratagene), with Superscript II reverse transcriptase (GIBCO/BRL) and dT primer (Boehringer Mannheim), subsequently the terminal of said cDNA was blunted. F linker shown in FIG. 1 and A linker shown in FIG. 2 were bound to the both terminals of cDNA obtained from normal fertilized and androgenetic embryos, respectively. Both F linker and A linker are constructed with complementary 17 mer and 20 mer oligo DNA, and 5'-terminal of 17 mer was phosphorylated. Each of the base sequences of F linker and A linker are described in Seq. ID No. 7 to 10 in the sequence listing.

(Amplification by PCR)

With primers complementary to 17 mer and 20 mer oligo DNA used for said linkers, cDNA library was amplified by PCR. cDNA was added to 100 µl of reaction mixture [a solution containing 20 mM Tris HCl, 10 mM KCl, 6 mM $(NH_4)_2SO_4$, 3.5 mM $MgCl_2$, 0.1% Triton X-100, 10 mM bovine serum albumin, all four dNTPs (120 µM each), 80 pmol primer complementary to each linker, and 2.5 unit of Pfu DNA polymerase (Stratagene) at the final concentration; pH 8.2]. Amplification consisted of a total of 30 cycles of thermal denaturation at 96° C. for 5 sec, annealing at 65° C. for 1 min, and extension reaction at 72° C. for 10 min was conducted with Perkin-Elmer GeneAmp PCR system 9600. After the amplification, subtraction-hybridization was carried out as previously described (Nat. Genet. 11, 52-59, 1995).

(Subtraction-Hybridization Method)

Three cycles of subtractions were repeatedly carried out using 10 ng cDNA of normal fertilized embryos, 1 µg cDNA of biotinylated androgenetic embryos, and magnetic beads, and concentrated cDNA was obtained. By hybridizing cDNA library of normal fertilized embryos with said cDNA as a probe, some Meg1 cDNA clones with various lengths that are expressed only from maternal genomes were isolated. Among the Meg1 cDNAs, the longest one was 5.4 kb. Judging from the determined base sequence of this cDNA, Meg1 was identified to be Grb10, however, it was revealed that there was a lack of 75 bp (25 amino acids), in comparison to the foregoing sequence reported by Ooi et al.

EXAMPLE 2 [GENERATION OF A TRANSGENIC MOUSE]

(Construction of a Transgene)

Figure 3:
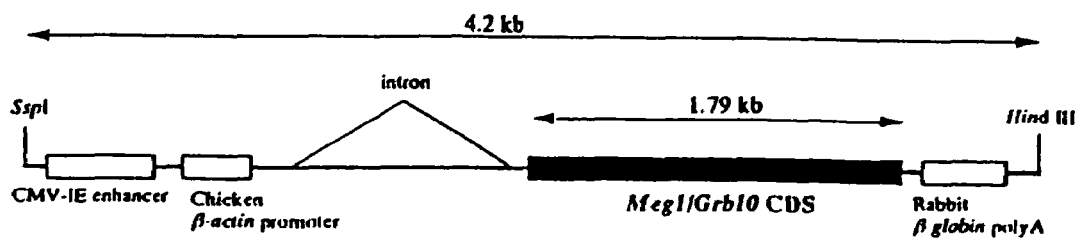
FIG. 3 is a view showing the structure of the transgene of a Meg1/Grb10 transgenic mouse of the present invention.

The obtained Meg1/Grb10 gene cDNA was inserted into XhoI site of a vector pCAGGS, a gift from Dr. Junichi Miyazaki of Osaka University Medical School, containing a CMV-IE enhancer, a chicken β-actin promoter and a rabbit β-globin poly A signal (Gene 108, 193-200, 1991), subsequently cut by restriction enzymes of SspI and HindIII to construct a 4.2 kb transgene, shown in FIG. 3, containing a CMV-IE enhancer, a chicken β-actin promoter, a 1.79 kb Meg1/Grb10 cDNA and a rabbit β-globin poly A signal, from 5'-terminal side.

(Construction of a Transgenic Mouse)

The aforementioned transgene was dissolved into phosphate buffered saline (PBS) to be 1000 copies/pl, and 2 pl of this DNA solution was microinjected into a male pronucleus of a fertilized egg (an early embryo; day 0.5) obtained from mating between B6C3H mice. This egg was cultured at 37° C. in M16 medium until two-celled stage, and transplanted into an oviduct of a pseudopregnant mouse (ICR strain) for ontogenesis, and then a transgenic mouse was born by Caesarean section. This obtaint transgenic mouse was immediately taken to foster parent (a female mouse that gave birth around the same time) to be raised until the weaning period. A tail of the transgenic mouse was cut by 5 mm at 1 to 3 weeks of age, and genomic DNA was extracted. The transgene was verified by PCR using a primer that specifically detects the introduced Meg1/Grb10 cDNA.

(Diabetic-Prone Transgenic Mouse)

Among the 5 strains of the transgenic mice constructed, 4 strains exhibited postnatal growth retardation, and 1 strain exhibited pre- and postnatal growth retardation and neonatal fatality. The incidence of diabetes was examined as to 2 (10 l, 18 L) of 5 strains. Diagnosis of diabetes was made by a measurement of glucose level in urine: urine of a mouse was placed on a piece of test paper for measuring glucose level in human urine, Hemacombistix (Bayer-Sankyo Co., Ltd.), and a level of color change was judged. The judgment was made in 4 scales of – (negative), + (false positive), ++ (positive) and ++++ (positive), according to the level of color change. Most of mice diagnosed as diabetes exhibited the scale of (++++). Further, diagnosis of diabetes was also made by measuring glucose level in blood which had been collected from the foot of an eyeball or a tail, with Glutest Ace (Sanwa Kagaku Kenkyusho Co., Ltd.). Mice that exhibited glucose level of 200 mg/dl or more were diagnosed as diabetes. Most of mice diagnosed as diabetes exhibited glucose level of 400 mg/dl or more.

Glycosuria began to be detected in the transgenic mice of the above-mentioned 2 strains after the mice became 3 months old. With regard to the mice of 1 strain (18 L), 70% or more of the male mice, heterozygous for the transgene, exhibited glycosuria and hyperglycemia before reaching 8 months old. The mice with early onset showed extremely severe symptoms, and a number of them died as early as about 2 months after the onset. The mice with late onset showed extremely high level of glucose in both urine and blood, however, they grew up healthily in appearance. As to female mice, there were only 2 mice judged as false positive (* in Table 1), and no mouse was diagnosed as diabetes. Among the male mice of the other strain (10 l ), the mice heterozygous for the transgene exhibited slight anomaly in the glucose level in urine and blood, but the mice homozygous for the transgene exhibited early onset of fulminant diabetes. The incidence of diabetes in the transgenic mice of these 2 strains is shown in Table 1.

TABLE 1

| strain | <3 months | % | <6 months | % | >6 months | % |
|---|---|---|---|---|---|---|
| 10l male | 15/72 | 20.8 | 17/72 | 23.6 | 18/72 | 25.0 |
| 10l female | 0/44 | 0.0 | 0/44 | 0.0 | 0/17 | 0.0 |
| 18L male | 13/38 | 34.2 | 24/38 | 63.2 | 27/38 | 71.1 |
| 18L female | 0/26 | 0.0 | *2/26 | (7.7) | | |

*false positive individuals

INDUSTRIAL APPLICABILITY

The present invention makes it possible to conduct a screening of a novel remedy for diabetes by using a mouse Meg1/Grb10 gene or a human GRB10 gene. Further, the transgenic non-human mammal such as the Meg1/Grb10 transgenic mouse or the GRB10 transgenic mouse of the present invention can be used as model animals for diabetes caused by a blockage of signal transductin from insulin and are useful for elucidating the onset mechanism and for the development of a novel remedy for diabetes.

What is claimed is:

1. A transgenic mouse comprising a Meg 1/Grb10 transgene encoding a protein comprising the amino acid sequence set forth in SEQ ID NO:2, wherein said mouse exhibits glucosuria and/or hyperglycemia.

2. The transgenic mouse according to claim 1, wherein the Meg1/Grb10 gene is a mouse Meg1/Grb10 gene comprising the DNA sequence set forth in SEQ ID NO:1.

3. The transgenic mouse according claim 1, wherein the transgene contains a chicken β-actin promoter, the Meg1/Grb10 gene and a rabbit β-globin poly A signal, which are sequenced in the order as recited.

4. The transgenic mouse according to claim 3, wherein the transgene containing a chicken β-actin promoter, the Meg1/Grb10 gene and a rabbit β-globin poly A signal, which are sequenced in this order, is the DNA sequence set forth in SEQ ID NO:3.

5. A method of generating a transgenic mouse characterized in comprising the steps of: (a) constructing a transgene containing cDNA that encodes a Meg1/Grb10 protein comprising SEQ ID NO: 2 downstream of a chicken β-actin promoter and upstream of a rabbit β-globin poly A signal, and subsequently microinjecting the transgene into a male pronucleus of a mouse fertilized egg; (b) culturing the egg cell microinjected with the transgene and then transplanting the cultured egg cell into an oviduct of a pseudopregnant female mouse; and (c) selecting baby mice comprising the transgene from mice born from the recipient female mouse produced in (b).

6. The method according to claim 5, wherein the transgene comprises the DNA sequence set forth as SEQ ID NO: 3.

7. A screening method of a remedy for diabetes characterized in using a meg1/grb10 gene, wherein the transgenic mouse according to claim 1 is used and wherein a subject material is administered to the transgenic mouse and the level of glucose in urine and/or blood obtained from the transgenic mouse is measured.

* * * * *